US012154239B2

(12) United States Patent
Papar

(10) Patent No.: US 12,154,239 B2
(45) Date of Patent: Nov. 26, 2024

(54) LIVE SURGICAL AID FOR BRAIN TUMOR RESECTION USING AUGMENTED REALITY AND DEEP LEARNING

(71) Applicant: Rayhan Papar, The Woodlands, TX (US)

(72) Inventor: Rayhan Papar, The Woodlands, TX (US)

( * ) Notice: Subject to any disclaimer, the term of this patent is extended or adjusted under 35 U.S.C. 154(b) by 0 days.

(21) Appl. No.: 18/433,236

(22) Filed: Feb. 5, 2024

(65) Prior Publication Data

US 2024/0265645 A1    Aug. 8, 2024

Related U.S. Application Data

(60) Provisional application No. 63/483,200, filed on Feb. 3, 2023.

(51) Int. Cl.
*G06T 19/00* (2011.01)
*G06K 15/12* (2006.01)
(Continued)

(52) U.S. Cl.
CPC ........ *G06T 19/006* (2013.01); *G06K 15/1276* (2013.01); *G06T 5/50* (2013.01);
(Continued)

(58) Field of Classification Search
CPC .................... G06T 19/006; G06T 5/50; G06T 2207/20221; G06T 2207/30096;
(Continued)

(56) References Cited

U.S. PATENT DOCUMENTS 10,088,544 B2 * 10/2018 Cetingul .......... G01R 33/56341
2010/0240988 A1    9/2010 Varga
(Continued)

FOREIGN PATENT DOCUMENTS

| AU | 2022252723 | 11/2022 |
|---|---|---|
| CA | 3107582 | 1/2020 |

(Continued)

OTHER PUBLICATIONS

U.S. Appl. No. 10/740,966, filed Aug. 11, 2020, Tong Chen.
(Continued)

*Primary Examiner* — Ryan R Yang
(74) *Attorney, Agent, or Firm* — Hoffberg & Associates; Steven M. Hoffberg

(57) ABSTRACT

An augmented reality system and method, comprising: a memory configured to store 3D medical scans comprising an image of a tumor and an angiogram; an output port configured to present a signal for presentation of an augmented reality display to a user; at least one camera, configured to capture images of a physiological object from a perspective; at least one processor, configured to: implement a first neural network trained to automatically segment the tumor; implement a second neural network to segment vasculature in proximity to the tumor; implement a third neural network to recognize a physiological object in the captured images; and generate an augmented reality display of the physiological object, tumor and vasculature based on the captured images, the segmented tumor and the segmented vasculature, compensated for changes in the perspective.

20 Claims, 14 Drawing Sheets

(51) Int. Cl.
  *G06T 5/50* (2006.01)
  *G06V 20/69* (2022.01)
  *G06V 20/70* (2022.01)
  *G16H 30/20* (2018.01)
  *G16H 30/40* (2018.01)

(52) U.S. Cl.
  CPC ............ *G06V 20/695* (2022.01); *G06V 20/70* (2022.01); *G16H 30/20* (2018.01); *G16H 30/40* (2018.01); *G06T 2207/20221* (2013.01); *G06T 2207/30096* (2013.01); *G06T 2207/30101* (2013.01); *G06V 2201/03* (2022.01); *G06V 2201/07* (2022.01)

(58) Field of Classification Search
  CPC ...... G06T 2207/30101; G06K 15/1276; G06V 20/695; G06V 20/70; G06V 2201/03; G06V 2201/07; G16H 30/20; G16H 30/40
  See application file for complete search history.

(56) References Cited

U.S. PATENT DOCUMENTS

| | | | |
|---|---|---|---|
| 2019/0011703 A1 | 1/2019 | Robaina | |
| 2019/0142519 A1 | 5/2019 | Siemionow | |
| 2019/0175285 A1 | 6/2019 | Siemionow | |
| 2019/0192230 A1 | 6/2019 | Siemionow | |
| 2019/0209116 A1* | 7/2019 | Sjöstrand | G16H 50/30 |
| 2020/0168334 A1 | 5/2020 | Mowery | |
| 2020/0311932 A1* | 10/2020 | Hooper | G06F 18/2413 |
| 2020/0327721 A1 | 10/2020 | Siemionow | |
| 2020/0342600 A1* | 10/2020 | Sjöstrand | A61B 6/032 |
| 2020/0405397 A1 | 12/2020 | Liu | |
| 2021/0045838 A1 | 2/2021 | Bradbury | |
| 2021/0103340 A1 | 4/2021 | Bradski | |
| 2021/0145642 A1 | 5/2021 | Berlin | |
| 2021/0161596 A1 | 6/2021 | Gurevich | |
| 2021/0201565 A1 | 7/2021 | Dibra | |
| 2021/0307841 A1 | 10/2021 | Buch | |
| 2021/0361483 A1 | 11/2021 | Berlin | |
| 2022/0062047 A1 | 3/2022 | Berlin | |
| 2022/0148459 A1 | 5/2022 | Stone | |
| 2022/0192776 A1* | 6/2022 | Gibby | A61B 1/000094 |
| 2022/0230310 A1* | 7/2022 | Xie | G06T 7/70 |
| 2022/0346884 A1 | 11/2022 | Leiderman | |
| 2023/0027518 A1 | 1/2023 | Bowman | |
| 2023/0252634 A1* | 8/2023 | Li | A61B 34/30 382/128 |

FOREIGN PATENT DOCUMENTS

| | | | |
|---|---|---|---|
| CA | 3176333 | 11/2021 | |
| CN | 102842122 | 12/2012 | |
| CN | 109982741 A * | 7/2019 | A61B 5/0042 |
| CN | 110338852 | 10/2019 | |
| CN | 111260786 | 6/2020 | |
| CN | 111325750 A * | 6/2020 | G06F 18/253 |
| CN | 112043378 | 12/2020 | |
| CN | 113796956 | 12/2021 | |
| CN | 113993475 | 1/2022 | |
| CN | 113994380 | 1/2022 | |
| CN | 114948199 | 8/2022 | |
| CN | 115049806 | 9/2022 | |
| EP | 3443888 | 2/2019 | |
| EP | 3443924 | 2/2019 | |
| EP | 3498212 | 6/2019 | |
| EP | 3726466 | 10/2020 | |
| EP | 3790491 | 3/2021 | |
| EP | 3826525 | 6/2021 | |
| EP | 3847628 | 7/2021 | |
| EP | 3920081 | 12/2021 | |
| EP | 3971907 | 3/2022 | |
| EP | 3993743 | 5/2022 | |
| EP | 4069129 | 10/2022 | |
| FR | 3110763 | 11/2021 | |
| FR | 3110764 | 11/2021 | |
| JP | 2021194544 | 12/2021 | |
| JP | 2022538906 | 9/2022 | |
| KR | 102180135 | 12/1899 | |
| KR | 20200041697 | 4/2020 | |
| KR | 20210014705 | 2/2021 | |
| KR | 20220038361 | 3/2022 | |
| KR | 102395505 | 5/2022 | |
| KR | 20230013041 | 1/2023 | |
| KR | 20230013042 | 1/2023 | |
| TW | 202248962 | 12/2022 | |
| WO | WO20220200572 | 12/1899 | |
| WO | WO2019165430 | 8/2019 | |
| WO | WO2019217893 | 11/2019 | |
| WO | WO2020023740 | 1/2020 | |
| WO | WO2020056532 | 3/2020 | |
| WO | WO2021003304 | 1/2021 | |
| WO | WO2021112988 | 6/2021 | |
| WO | WO2021214750 | 10/2021 | |
| WO | WO2021234304 | 11/2021 | |
| WO | WO2021234305 | 11/2021 | |
| WO | WO2021245212 | 12/2021 | |
| WO | WO2021252384 | 12/2021 | |
| WO | WO2022014255 | 1/2022 | |
| WO | WO2022060409 | 3/2022 | |
| WO | WO2022079251 | 4/2022 | |
| WO | WO-2022241121 A1 * | 11/2022 | G06T 7/11 |
| WO | WO2023004299 | 1/2023 | |

OTHER PUBLICATIONS

U.S. Appl. No. 10/937,542, filed Mar. 2, 2021, Gokce Yildirim.
U.S. Appl. No. 11/071,647, filed Jul. 27, 2021, Michael S. Berlin.
U.S. Appl. No. 11/278,359, filed Mar. 22, 2022, Krzysztof B. Siemionow.
Ayoub, Ashraf, and Yeshwanth Pulijala. "The application of virtual reality and augmented reality in Oral & Maxillofacial Surgery." BMC Oral Health 19 (2019): 1-8.
Best, J. (2018). Augmented reality in the operating theater: How surgeons are using Microsoft's HoloLens to make operations better. ZDNET.
Brain Tumor: Statistics. (2022). Cancer.Net. www.cancer.net/cancer-types/brain-tumor/statistics.
Chidambaram, Swathi, Vito Stifano, Michelle Demetres, Mariano Teyssandier, Maria Chiara Palumbo, Alberto Redaelli, Alessandro Olivi, Michael LJ Apuzzo, and Susan C. Pannullo. "Applications of augmented reality in the neurosurgical operating room: a systematic review of the literature." Journal of Clinical Neuroscience 91 (2021): 43-61.
Djenouri, Youcef, Asma Belhadi, Gautam Srivastava, and Jerry Chun-Wei Lin. "Secure collaborative augmented reality framework for biomedical informatics." IEEE Journal of Biomedical and Health Informatics 26, No. 6 (2021): 2417-2424.
Fick, Tim, Jesse AM van Doormaal, Lazar Tosic, Renate J. van Zoest, Jene W. Meulstee, Eelco W. Hoving, and Tristan PC van Doormaal. "Fully automatic brain tumor segmentation for 3D evaluation in augmented reality." Neurosurgical focus 51, No. 2 (2021): E14.
González izard, Santiago, Juan A. Juanes Méndez, Pablo Ruisoto Palomera, and Francisco J. García-Peñalvo. "Applications of virtual and augmented reality in biomedical imaging." Journal of medical systems 43 (2019): 1-5.
Haouchine, Nazim, Parikshit Juvekar, Michael Nercessian, William M. Wells III, Alexandra Golby, and Sarah Frisken. "Pose estimation and non-rigid registration for augmented reality during neurosurgery." IEEE Transactions on Biomedical Engineering 69, No. 4 (2021): 1310-1317.
Hollon, Todd C., Balaji Pandian, Arjun R. Adapa, Esteban Urias, Akshay V. Save, Siri Sahib S. Khalsa, Daniel G. Eichberg et al. "Near real-time intraoperative brain tumor diagnosis using stimulated Raman histology and deep neural networks." Nature medicine 26, No. 1 (2020): 52-58.

(56) References Cited

OTHER PUBLICATIONS

Huang, James, Martin Halicek, Maysam Shahedi, and Baowei Fei. "Augmented reality visualization of hyperspectral imaging classifications for image-guided brain tumor phantom resection." In Medical Imaging 2020: Image-Guided Procedures, Robotic Interventions, and Modeling, vol. 11315, pp. 206-215. SPIE, 2020.

Jasenovcova, L. (2022). What is augmented reality and how does AR work. Resco. www.resco.net/blog/what-is-augmented-reality-and-how-does-ar-work/.

Johns Hopkins Performs Its First Augmented Reality Surgeries in Patients. (2021). Johns Hopkins Medicine. www.hopkinsmedicine.org/news/articles/johns-hopkins-performs-its-first-augment ed-reality-surgeries-in-patients.

Jud, Lukas, Javad Fotouhi, Octavian Andronic, Alexander Aichmair, Greg Osgood, Nassir Navab, and Mazda Farshad. "Applicability of augmented reality in orthopedic surgery—a systematic review." BMC musculoskeletal disorders 21, No. 1 (2020): 1-13. bmcmusculoskeletdisord.biomedcentral.com/articles/10.1186/s12891-020-3110-2.

Le, J. (2021). How to do Semantic Segmentation using Deep Learning. Nanonets. nanonets.com/blog/how-to-do-semantic-segmentation-using-deep-learning/.

Lee, Chester, and George Kwok Chu Wong. "Virtual reality and augmented reality in the management of intracranial tumors: a review." Journal of Clinical Neuroscience 62 (2019): 14-20.

Lee, Tae-Ho, Viduranga Munasinghe, Yan-Mei Li, Jiajie Xu, Hyuk-Jae Lee, and Jin-Sung Kim. "GAN-Based Medical Image Registration for Augmented Reality Applications." In 2022 IEEE 4th International Conference on Artificial Intelligence Circuits and Systems (AICAS), pp. 279-282. IEEE, 2022.

Liu, Tao, Yonghang Tai, Chengming Zhao, Lei Wei, Jun Zhang, Junjun Pan, and Junsheng Shi. "Augmented reality in neurosurgical navigation: a survey." The International Journal of Medical Robotics and Computer Assisted Surgery 16, No. 6 (2020): 1-20.

Lungu, Abel J., Wout Swinkels, Luc Claesen, Puxun Tu, Jan Egger, and Xiaojun Chen. "A review on the applications of virtual reality, augmented reality and mixed reality in surgical simulation: an extension to different kinds of surgery." Expert review of medical devices 18, No. 1 (2021): 47-62.

Malhotra, Priyanka, Sheifali Gupta, Deepika Koundal, Atef Zaguia, and Wegayehu Enbeyle. "Deep neural networks for medical image segmentation." Journal of Healthcare Engineering 2022 (2022).

McKnight, R. Randall, Christian A. Pean, J. Stewart Buck, John S. Hwang, Joseph R. Hsu, and Sarah N. Pierrie. "Virtual reality and augmented reality-translating surgical training into surgical technique." Current Reviews in Musculoskeletal Medicine 13 (2020): 663-674.

Meola, A., Cutolo, F., Carbone, M., Cagnazzo, F., Ferrari, M., & Ferrari, V. (2017). Augmented Reality in Neurosurgery: A Systematic Review. Neurosurgical Review, 40(4), 537-548. doi.org/10.1007/s10143-016-0732-9.

Mikhail, Mirriam, Karim Mithani, and George M. Ibrahim. "Presurgical and intraoperative augmented reality in neuro-oncologic surgery: clinical experiences and limitations." World neurosurgery 128 (2019): 268-276.

Minimally Invasive Brain Tumor Surgery. (2022). Pacific Neuroscience Institute. www.pacificneuroscienceinstitute.org/brain-tumor/treatment/minimally-invasive-brain-surgery/#tab-gravity-assisted.

Montemurro, Nicola, Sara Condino, Marina Carbone, Nadia Cattari, Renzo D'Amato, Fabrizio Cutolo, and Vincenzo Ferrari. "Brain Tumor and Augmented Reality: New Technologies for the Future." International Journal of Environmental Research and Public Health 19, No. 10 (2022): 6347.

Ponnusamy, Vijayakumar, J. Christopher Clement, K. C. Sriharipriya, and Sowmya Natarajan. "Smart healthcare technologies for massive internet of medical things." In Efficient Data Handling for Massive Internet of Medical Things: Healthcare Data Analytics, pp. 71-101. Cham: Springer International Publishing, 2021.

Salehahmadi, F., & Hajialiasgari, F. (2019). Grand Adventure of Augmented Reality in Landscape of Surgery. World Journal of Plastic Surgery, 8(2). doi.org/10.29252/wjps.8.2.135.

Satoh, Makoto, Takeshi Nakajima, Takashi Yamaguchi, Eiju Watanabe, and Kensuke Kawai. "Evaluation of augmented-reality based navigation for brain tumor surgery." Journal of Clinical Neuroscience 94 (2021): 305-314.

Siegel, R., L., Miller, K., D., Fuchs, H., E., & Jemal, A. (2021). Cancer Statistics 2021. Cancer Journal for Clinicians, 71(1), 7-33. doi.org/10.3322/caac.21654.

Surgery for Brain Tumours. (2019). Cancer Research UK. www.cancerresearchuk.org/about-cancer/brain-tumours/treatment/surgery/remove- brain-tumour.

Van Doormaal, Jesse AM, Tim Fick, Meedie Ali, Mare Köllen, Vince van der Kuijp, and Tristan PC van Doormaal. "Fully automatic adaptive meshing based segmentation of the ventricular system for augmented reality visualization and navigation." World Neurosurgery 156 (2021): e9-e24.

What is Deep Learning? (n.d.). Mathworks. Retrieved Sep. 26, 2022 from www.mathworks.com/discovery/deep-learning.html.

Geoslam "What is SLAM (Simultaneous Localization and Mapping)?" Retrieved Sep. 26, 2022 from geoslam/us/what-is-slam/.

www.zdnet.com/article/augmented-reality-in-the-operating-theatre-how-surgeons- are-using-microsofts-hololens-to-make/.

S.H. Tang, "Review: 3D U-Net—Volumetric Segmentation," 2019, Towards Data Science. medium.com/towards-data-science/review-3d-u-net-volumetric-segmentation-medical-image-segmentation-8b592560fac 1.

H. Zhang, L. Xia, J. Yang, H. Hao, J. Liu, Y. Zhao, "Cerebrovascular Segmentation in MRA via Reverse Edge Attention Network," 2020, MICCAI 2020, 12266(1), p. 66-75 (doi.org/10.1007/978-3-030-59725-2_7).

\* cited by examiner

RE-NET

REAM

LIVE SURGICAL AID FOR BRAIN TUMOR RESECTION USING AUGMENTED REALITY AND DEEP LEARNING

CROSS REFERENCE TO RELATED APPLICATIONS

The present application is a Non-provisional of, and claims benefit of priority under 35 U.S.C. § 1.119(e), of U.S. Provisional Patent Application No. 63/483,200, filed Feb. 3, 2023, the entirety of which is expressly incorporated herein by reference.

COPYRIGHT NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

BACKGROUND OF THE INVENTION

Craniotomy is the standard procedure for brain tumor resection, but in recent years, the development of minimally invasive surgery for this application has grown significantly. However, minimally invasive surgeries do have downsides—surgeons do not directly see the surgical site and are separated from preoperative scans in which the tumor location and other data is displayed, resulting in a loss of visual and haptic feedback.

In 2020, an estimated 308,000 people worldwide were diagnosed with brain cancer and of those people, 251,000 died (Siegel et al., 2021). Brain cancer is the tenth deadliest cancer for both men and women and only 36% of patients survive the five years following their diagnoses.

The most common treatment for brain cancer is surgical removal of the tumors through a craniotomy, and this is the only available treatment ("Brain Tumor", n.d.).

Recent developments in surgical technique have allowed for a minimally invasive approach to tumor resection as opposed to the standard craniotomy ("Surgery for Brain", n.d.). When compared with the craniotomy, these surgeries are much safer as they reduce the risk of infection and damaging brain matter ("Minimally Invasive", 2022). However, current systems for minimally invasive surgeries require surgeons to rely solely on two-dimensional (2D) external displays showing pre-operative scans, as well as a camera feed from the probe the surgeon uses to perform the surgery, as opposed to being able to directly see the patient's anatomy (Meola et al., 2017). This results in a loss of haptic feedback, the ability to create and feel pressure, possibly creating a disconnect with the surgery from being unable to see the surgical site in real life and having to rely on deciphering the location of the tumor from separate 2D screens (Meola et al., 2017). With all these issues, only experienced neurosurgeons and facilities with advanced technologies can perform minimally invasive tumor resections, and even still, the risks of damaging vascular or nervous tissue are high due to the visual disadvantages, the small surgical field, and the cognitive overload of the procedure on the surgeon (Meola et al., 2017).

To avoid the burden of switching perspectives and translating information from separate 2D screens to the real-life surgical site, a comprehensive neuronavigational system is needed to visualize all of the data in one place. Augmented reality (AR), a term used to describe the combination of real-life and computer-generated content, has been proposed and developed as a viable solution for certain minimally invasive operations that require precision with low visibility (Salehahmadi & Hajialiasgari, 2019). AR could be a beneficial utility to aid in brain tumor surgery by visualizing the tumor as well as nervous and vascular structures in one comprehensive 3D view.

AR through the use of a head-mounted display has been applied to surgeries. A recent surgery done at Johns Hopkins utilized AR for spinal fusion by displaying the exact positioning of the screws that were to be implanted into the spine on head-mounted AR goggles ("Johns Hopkins", 2021).

In recent years, the development of minimally invasive surgeries has allowed for reduced recovery time and risk of infection, however, they do have their downsides; surgeons do not directly see the surgical site and are separated from preoperative scans from which they get the tumor location and other necessary data, resulting in a loss of visual and haptic feedback. To aid this issue and significantly increase the safety of minimally invasive brain tumor resections, live surgical aids have been proposed utilizing AR.

Technologies, such as microscopes and endoscopes, have been developed to help surgeons combat some of the issues while performing minimally invasive operations. These utilities, however, separate the surgeon from the screens with preoperative scans, so the surgeon must continuously switch perspectives to be able to operate the tools.

Neuronavigation is the concept of using technology within surgery to navigate through patient anatomy. There are several utilities for neuronavigation, the most basic being the use of preoperative scans. Surgeons will utilize preoperative scans such as Magnetic Resonance Imaging (MRI) and Computed Tomography (CT), displayed on a separate screen to localize the tumor. In addition to this, some surgeries will utilize intraoperative scans, or scans taken during surgery. In some situations, surgeons will use 5-aminolevulinic acid (5-ALA), which concentrates in the cancerous cells of the tumor. This allows surgeons to see additional parts of the tumor that appear similar to healthy tissue in the brain.

To avoid the burden of switching perspectives and translating information from separate 2D screens to the real-life surgical site, a comprehensive neuronavigational system is needed to visualize all of the data in one place. AR is a term used to describe the combination of real-life and computer-generated content, has been proposed and developed as a viable solution for certain minimally invasive operations that require precision with low visibility (Salehahmadi & Hajialiasgari, 2019). AR could be a beneficial utility to aid in brain tumor surgery by visualizing the tumor as well as nervous and vascular structures in one comprehensive 3D view.

Deep learning uses a complex neural network, a series of interconnected layers that function similar to the human brain, to learn complex patterns within data, usually an image ("What is Deep Learning", n.d.). Deep learning involves both an algorithm, the neural network in this case, and data. Deep learning is best suitable for large amounts of data, and algorithms have hundreds of layers as opposed to standard machine learning networks that only contain a couple layers in the neural network ("What is Deep Learning", n.d.). Deep learning is often applied to computer vision, the task of interpreting an image, due to the large amounts of data in an image. In image processing, the goal is often to identify if there is an object in the photo, locate where the object is, or accurately outline the object in the image. Outlining an object in the image is often used in medical applications, for example outlining a tumor, and is known as segmentation. Segmentation is a resource-intensive process, and requires specialized deep neural networks known as Convolutional Neural Networks (CNN) (Le, 2021). A convolutional neural network is a special type of neural network that alters the image at each layer to make the data more manageable and to better understand the image. The performance of a CNN is dependent upon its architecture as well as the amount of data it is trained on; designing the optimal CNN using the various image convolution operations that exist can be a challenge.

Deep learning is also extensively used in augmented reality; accurately superimposing 3D models into real life requires CNNs that are able to pinpoint where a model should be placed in an image. AR requires three components: sensors, algorithms, and output devices (Jasenovcova, 2022). AR can utilize multiple positional sensors, such as GPS and gyro, as well as LiDAR for more accurate results, but basic superimposition requires only a single camera. The type of AR being performed determines the number of sensors needed. Marker-based AR requires only a camera and functions through locating a specific symbol, and then layering an object with reference to that symbol (Jasenovcova, 2022). Marker-based AR is very accurate, but it requires the use of a specific symbol to work, therefore, it is not applicable in all areas. Marker-less superimposition AR improves its accuracy with more sensors. This type of AR superimposes a 3D model or image on an object. The difference between the object and the marker is that the marker is easy to recognize, like a barcode or QR code, while the object could be anything, like a person. All types of AR require an algorithm, the actual artificial intelligence that is determining the location of the markers or objects and then overlaying the model in 3D (Jasenovcova, 2022). This algorithm is called simultaneous localization and mapping (SLAM) ("What is SLAM", n.d.). SLAM is able to generate 3D environments from its surroundings as well as localize itself in that environment through use of only a camera. SLAM allows for the 3D model projected and oriented the right way when displayed on the headset. As for the algorithm behind SLAM, it is composed of fine-tuned CNNs that are able to extrapolate 3D data from a single image through use of depth perception ("What is SLAM", n.d.). The CNN first recognizes the location where the augment must be displayed, this can be a marker akin to something resembling a QR code, or it can be an actual object like a person. After the system has identified that the marker or object is present, it must extract and locate the features from the object; for example, the AR system will first locate the person, and then locate the arms, legs, and head.

The AR system can accurately position the model over the features, such as superimposing a skeleton on a person. From here, the system repeatedly performs the same detection and positioning of the model, updating the headset display in real time.

AR through the use of a head-mounted display has been applied to surgeries. A recent surgery done at Johns Hopkins utilized AR for spinal fusion by displaying the exact positioning of the screws that were to be implanted into the spine on head-mounted AR goggles ("Johns Hopkins", 2021). Surgeons at St. Mary's hospital in London have also integrated AR into some of their surgical procedures by overlaying bones, muscles, and blood vessels onto the surgeon's field of view (Best, 2018). AR has also been applied to certain orthopedic surgeries, and surgeons who wore AR goggles were found to achieve a higher precision cut than those who did not (Jud et al., 2020).

For both traditional and minimally invasive procedures, AR had been proposed and tested on certain operations like spine surgery, but its application on cancer removal surgeries, specifically brain tumor resections, has yet to be developed and tested.

SUMMARY OF THE INVENTION

The present invention provides an AR system which transforms unlabeled 3D medical scans such as Magnetic Resonance Imaging (MRI) outputs into a comprehensive visualization of the tumor and peripheral structures in AR during tumor resection surgeries. The system employs both deep learning and AR. A deep learning model, using a 3D U-NET, was programmed and trained to automatically segment brain tumors in 3D from MRIs. A second deep learning model utilizing the RE-NET algorithm was constructed to segment cerebral vasculature from Magnetic Resonance Angiography (MRA). An algorithm was constructed to identify white matter tracts from diffusion tensor imaging volume utilizing Deterministic Maximum Direction Getter. The patient-specific 3D models were then implemented in Unity Engine and uploaded to a Windows-based head-mounted display device and superimposed in real-time onto a physical simulator head and medical instrument. This surgical aid provides three other AR visualization modes to further assist users, and features to ensure ease-of-use and adaptability in the surgical environment. This technology provides an intraoperative aid during surgery by providing a comprehensive visualization of the tumor, vascular, and nervous data, removing the need to switch perspectives between the surgical site and preoperative scans. This project can also be used as an effective aid in preoperative planning and surgical training.

The AR system first segments a tumor from preoperative MRI scans using a trained deep learning model and generates a 3D segmentation of the tumor. Then, cerebral vasculature is segmented from a MRA to create a comprehensive patient-specific 3D model. A third peripheral segmentation is also performed on patient-specific diffusion tensor imaging to identify vital white matter tracts. These generated 3D models are then uploaded into the Unity Engine. A tracking algorithm was designed to recognize spherical retroreflective markers that reflect light back towards its source. See FIG. 10.

This algorithm utilized data from the head-mounted display device's RGB stereoscopic cameras, time of Flight depth sensors, and inertial measurement units to identify said retroreflective markers and reconstruct them in a virtual 3D space. These retroreflective markers were placed on a patient head phantom. The generated 3D models of the cerebral anatomical structures were then superimposed by the detection algorithm onto the physical head, aided by the retroreflective markers placed on it. See FIG. 11.

The comprehensive surgical aid system also allowed for any combination of tumor, vasculature, white matter tract, and surgical resection path models to be visualized at any point, facilitated by user interface and voice recognition.

The 3D U-NET is the CNN used for brain tumor segmentation. This algorithm features two parts: an encoder and a decoder. The encoder comprises several layers of convolutions as well as max pooling every two convolutions. The decoder features layers of convolutions and up-convolutions or transpose convolutions every two convolution layers. This algorithm essentially reduces the features of an image through convolutions in the encoder, and then increases the features again in the decoder. The repeated change of the image through the weights of each layer allows for a segmentation map to be produced from the input image. The 3D U-NET additionally features skip connections to prevent degradation due to the depth of the algorithm. The skip connections transfer the convoluted image to the equally sized layers across the U-structure, essentially skipping a portion of the encoder and decoder. A diagram of the U-NET is shown in FIG. 1, from "Review: 3D U-Net—Volumetric Segmentation," by S. H. Tsang, 2019, Towards Data Science. medium.com/towards-data-science/review-3d-u-net-volumetric-segmentation-medical-image-segmentation-8b592560fac1

The Reverse Edge Attention Network (RE-Net) was the CNN used for cerebrovascular segmentation. This algorithm functions similar to the U-NET, as it features both an encoder and decoder, however this algorithm is more optimized for the specific application of blood vessel segmentation. The RE-Net also features skip connections, however a special operation known as the Reverse Edge Attention Module (REAM) is embedded in each skip connection to extract segmentation edges from the encoder. FIG. 2 depicts a diagram of the RE-Net, from "Cerebrovascular Segmentation in MRA via Reverse Edge Attention Network," by H. Zhang, L. Xia, J. Yang, H. Hao, J. Liu, Y. Zhao, 2020, MICCAI 2020, 12266(1), p. 66-75 (doi.org/10.1007/978-3-030-59725-2_7).

The Deterministic Maximum Direction Getter (DMDG) algorithm was implemented into the task of fiber tractography or identifying white matter pathways from diffusion tensor imaging. At each voxel representation of the brain, a diffusion tensor was calculated demonstrating the movement of water. Seed points, or regions of interest, were selected based on predefined points in proximity to major anatomical structures the DMDG algorithmically propagated through pathways to reconstruct a 3D model of the white matter tracts.

The segmented anatomical models are then uploaded into an AR application equipped with an advanced tracking algorithm utilizing the various sensors on the head-mounted display device. Retroreflective markers, commonly used in the field of motion tracking, are reapplied such that the head-mounted display can recognize specific arrangements of these spherical markers and superimpose the 3D models on them in a certain orientation. These spherical markers are attached to a stationary physical simulator head and a mobile medical instrument to simulate a surgical environment. The tracking algorithm first uses the Time-of-Flight depth sensor which utilizes infrared light to recognize depth to highlight the locations of retroreflective markers in 2D, as they appear significantly brighter due to their reflective properties. A blob detection algorithm is run on these frames in real-time to ensure that the bright spot is a marker. This data is then combined with the depth to create a 3D reconstruction of the markers. From this, the tracking algorithm determines the orientation of the markers and the position and rotation of the head-mounted display in relation to them. This 3D reconstruction is then used to superimpose the anatomical structures on the centroid of the marker cluster.

The AR application provides a suite of other functionality accessed through a specifically tailored user interface for seamless operation during surgical procedures. The first of these modes is the ability to expand the anatomical models and segmentations, detaching them from the patient head and allowing a more detailed examination of anatomical intricacies. The second mode facilitates the AR application of nervous mapping using the white matter tractography and full connectome obtained from diffusion tensor imaging. The third mode allows for the visualization of medical scans in three dimensions, either a single important slice or the full volume with a slider to choose a single slice.

This technology provides a comprehensive visualization of the tumor and surrounding vascular and nervous structures overlayed in correct positions and orientations on the patient to reduce the perceptual and cognitive burden of the surgery, maximize safety, and reduce risk of damage to surrounding tissue. The AR system can be effectively utilized for preoperative planning, medical and surgical training, and during surgical procedures.

The present technology provides a surgical live aid using AR and Deep Learning to reduce the risks during brain tumor resections. This system includes several sub-systems: Segmentation, AR, and Physical Markers. The Segmentation portion includes the deep learning models for brain tumor segmentation and cerebrovascular segmentation which generate the 3D models from unlabeled medical scans as well as the algorithms that extract white matter tractograms. The AR portion consists of rendering and displaying the tumor, vasculature, white matter tracts, with accurate visual shaders and the incorporation of user interface and voice recognition to easily control the models that are displayed and the mode of the surgical aid. The Physical Markers consist of the object upon which the 3D models will be superimposed, and the tracking algorithm used to recognize the retroreflective markers.

With the development of minimally invasive surgeries as a method for brain tumor resection, as opposed to the standard craniotomy, the risk of infection and recovery time has greatly decreased. However, minimally invasive surgeries do possess several disadvantages, such as the fact that the surgeon is separated from the surgical site, resulting in a loss of visual and haptic feedback. Additionally, the surgeon is separated from preoperative scans from which they get the position of the tumor and other data, in both minimally invasive surgeries and craniotomies. These disadvantages only allow for exceptionally skilled neurosurgeons to perform minimally invasive operations, and even still, they pose significant risks to the patient.

To address this issue and significantly increase the safety of brain tumor resections, a live surgical aid was constructed utilizing both deep learning and augmented reality. A deep learning model, using a 3D U-NET, was programmed and trained on the BraTS 2020 dataset to automatically segment brain tumors in 3D from MRIs. A second deep learning model utilizing the RE-NET algorithm was constructed and trained on the TubeTK Healthy MRA Database to segment cerebral vasculature from a Magnetic Resonance Angiography (MRA). A third deep learning model was then trained to recognize a physical target in real life, a 3D-printed head that would serve as the demonstration target for augmented reality.

The 3D models were then implemented and rendered in Unity and uploaded to an Android-based augmented reality headset. As shown in FIG. 12, a user wears an augmented reality headset (e.g., Microsoft HoloLens 2), and employs a smartphone as a user interface. The augmented reality headset visualizes the neural anatomy, vasculature, and tumor within the head of the patient, with correct perspective for the user.

The evaluation of this system was based on the segmentation accuracy of the brain tumor and cerebral vasculature, in which their models returned Diverse Counterfactual Explanation (DICE) scores of 0.69 and 0.75, respectively, signifying exceptional accuracy. The thresholds that were used to produce each binary mask were then optimized using an Receiver Operating Characteristic (ROC) curve and a Precision-Recall Curve, producing significantly more accurate predictions.

In order to present the images to a user, the image may be defined by translucent elements and opaque elements. The elements may be depth encoded, so that the opacity of the elements change with depth. That is, tissues in front of the tumor or region of interest are translucent, while those behind are opaque, to help unclutter the display. In general, in the case of a tumor and vasculature, the tumor is presented as an opaque bounded region or regions, while the vasculature in front of the tumor is translucent. The brain mass and important tracts in front of the tumor are also translucent, while behind the plane of the tumor with respect to the viewer, the layers may have increasing opacity. In some cases, critical tissues such as major arteries may be opaque, while minor vessels are translucent.

As a procedure progresses, the tissue coding may be modified. As a simplified example, because the tumor is visualized as a virtual object in the viewport, removal of the tumor during the procedure does not necessarily result in a visual reduction in the tumor volume. Therefore, the real time video feed is analyzed to determine changes in the tissue during the procedure, and the virtual objects may be updated to represent the physical changes.

Further, during initial access to the tissue for a subsurface tumor, the tumor itself need not be visualized, allowing the surgeon to assess the vasculature in a simplified interface. After a path to the tumor is created, the tumor boundaries may be visualized.

In case of uncontrolled bleeding or oozing, the real time camera feed may be analyzed to help isolate the source(s) of bleeding, which in some cases may be unclear, with the areas of interest coded in the user interface.

The technology has extensive application, the main purpose being intended for the live and intraoperative use in craniotomies and minimally invasive resections. Surgeons can wear the AR headsets to be able to clearly see an adjustable and comprehensive visualization of the position of the tumor, blood vessels, and other data. This removes the need for the surgeon to constantly switch perspectives, between the surgical site/endoscope feed and the separate 2D screens. This AR surgical aid can also be used for preoperative planning, as rendering the tumor, vasculature, white matter tracts, etc. in 3D will allow for more effective planning and collaboration. A third important application of this surgical aid and AR in general is its use in medical training, so medical students can visualize how the surgery occurs through a more interactive experience.

It is therefore an object of the invention to provide an augmented reality method, comprising: storing 3D medical scans comprising a tumor image, a diffusion tensor image, and an angiogram; capturing images of a physiological object from a perspective; automatically segmenting the tumor image with a first neural network; automatically segmenting white matter pathways in a 3D brain scan; automatically segmenting vasculature in proximity to the tumor with a second neural network; automatically recognizing a physiological object in the captured images with a third neural network; defining depth coded layers having opacity; generating an augmented reality display of the physiological object, white matter, tumor, and vasculature based on the captured images, the segmented tumor, the segmented vasculature, and the white matter pathways, dependent on the depth coded layers having opacity and dynamic changes in the perspective; and presenting the augmented reality display to the user.

It is also an object to provide an augmented reality system, comprising: a memory configured to store at least one type of medical image of an anatomical region; at least one camera configured to capture images of anatomy from a dynamically changing perspective; at least one processor configured to: receive the images of the at least one type of medical image; receive the captured images; segment the at least one type of medical image; implement an object recognition neural network trained to recognize the anatomical region in the captured images; and generate an augmented reality representation of the at least one type of medical image merged with the anatomical region from the dynamically changing perspective; and an output port configured to present the augmented reality representation.

The at least one type of medical image may comprise a 3D angiogram type of medical image, a 3D diffusion tensor image, and a 3D tumor type of medical image.

The segmenting of the at least one type of medical image may be performed by a plurality of segmenting neural networks comprising a first segmenting neural network configured to distinguish vascular tissue from nonvascular tissue, and a second segmenting neural network configured to distinguish tumor tissue from nontumor tissue.

The at least one type of medical image may comprise a white matter tractogram.

The at least one processor may be configured to reconstruct a 3D model of the white matter tracts from diffusion tensor imaging using a Deterministic Maximum Direction Getter (DMDG) algorithm.

The anatomical region may be a cranium; and the least one type of medical image may comprise: a first type of medical image selected from the group consisting of at least one of a magnetic resonance angiogram and a computed tomography angiogram; a second type of medical image comprising a magnetic resonance image; and a third type of medical image comprising a diffusion tensor image.

The at least one segmenting neural network may comprise a 3D U-NET, having at least a convolutional neural network, an encoder and a decoder. The encoder may comprise a plurality of layers of convolutions, with max pooling over multiple convolution layers, and the decoder comprises a plurality of layers of convolutions with up-convolutions or transpose convolutions over multiple convolution layers.

The object recognition neural network may comprise a Reverse Edge Attention network (RE-NET) with skip connections, with a Reverse Edge Attention Module (REAM) embedded in each skip connection. The at least one processor may be configured to generate the augmented reality representation by recognition of at least one physical marker of the anatomical region, and superimposition of the segmented at least one type of medical image on the captured images.

The at least one processor may be further configured to recognize at least one retroreflective marker on a surface of the anatomical region, and to dynamically track position and orientation of the anatomical region with respect to the at least one camera based on the recognized at least one retroreflective marker.

The augmented reality representation may comprise a haptic output configured to produce proprioceptive stimulation corresponding to a virtual boundary condition according to the segmented at least one type of medical image.

It is also an object to provide an augmented reality system, comprising: a memory configured to store data from volumetric medical images comprising a plurality of image types of characteristics of an anatomical region; an augmented reality user interface comprising at least one camera, at least one inertial sensor, and a display configured to overlay a computer generated image on a live action image; at least one automated processor, configured to: determine a viewport of the augmented reality user interface; recognize a location and an orientation of an anatomical region in the viewport in realtime; overlay a representation of the stored data on the viewport; and control the augmented reality user interface.

The volumetric medical images may comprise at least a 3D angiogram and a white matter track image. The at least one automated processor may be further configured to segment at least one of the volumetric medical images using at least one neural network, and to overlay the segmented volumetric medical images on the viewport. The volumetric medical images may further comprise a magnetic resonance image of a brain tumor, and the at least one automated processor is further configured to segment the 3D angiogram to distinguish arteries, segment the magnetic resonance image to distinguish the brain tumor, label elements as foreground and background, and to apply obscuring logic based on relative depth. The at least one automated processor may be further configured to segment the 3D angiogram and segment the magnetic resonance image of the brain tumor with a 3D U-NET, having at least a convolutional neural network, an encoder with max pooling and a decoder with up-convolutions or transpose convolutions, wherein the 3D U-NET further comprises skip connections, which transfer a convoluted image to the equally sized layers across a U-structure, skipping a portion of the encoder and decoder. The object recognition neural network may comprise a Reverse Edge Attention network (RE-NET) with skip connections, having a Reverse Edge Attention Module (REAM) embedded in each skip connection. The at least one automated processor may be further configured to process the stored data to reconstruct a 3D model of white matter tracts from diffusion tensor imaging using a Deterministic Maximum Direction Getter (DMDG) algorithm. The at least one automated processor may be further configured to recognize at least one visible physical marker of the anatomical region, and superimpose the segmented at least one type of medical image on the captured images.

The augmented reality system may further comprise a haptic interface configured to provide tactile feedback representing at least segmentation boundaries of at least one image type.

It is therefore an object to provide an AR system, comprising: a memory configured to store 3D medical scans comprising an image of a tumor, angiogram, and white matter; an output port configured to present a signal for presentation of an AR display to a user; at least one camera, configured to capture images of a physiological object from a perspective; at least one processor, configured to: implement a first neural network trained to automatically segment the tumor; implement a second neural network to segment vasculature in proximity to the tumor; implement an algorithm to segment white matter in proximity to the tumor; implement a tracking algorithm to recognize a physiological object in the captured images; and generate an AR display of the physiological object, tumor, vasculature, and white matter based on the captured images, the segmented tumor and the segmented vasculature, compensated for changes in the perspective.

It is also an object to provide an AR method, comprising: storing 3D medical scans comprising an image of a tumor, angiogram, and white matter; capturing images of a physiological object from a perspective; implementing a first neural network trained to automatically segment the tumor; implementing a second neural network to segment vasculature in proximity to the tumor; implementing an algorithm to segment white matter in proximity to the tumor; implementing a tracking algorithm to recognize a physiological object in the captured images; generating an AR display of the physiological object, tumor and vasculature based on the captured images, the segmented tumor, the segmented vasculature, and the segmented white matter, compensated for changes in the perspective; and presenting the AR display to the user.

It is a further object to provide a nontransitory computer readable medium for controlling a programmable system to perform an AR method, comprising: instructions for capturing images of a physiological object from a perspective; instructions for implementing a first neural network trained to automatically segment a tumor from a 3D medical image; instructions for implementing a second neural network to segment vasculature in proximity to the tumor from a 3D angiogram image; instructions for implementing an algorithm to segment white matter in proximity to the tumor from a diffusion MRI; instructions for implementing a tracking algorithm to recognize a physiological object in the captured images; instructions for generating an AR display of the physiological object, tumor and vasculature based on the captured images, the segmented tumor and the segmented vasculature, compensated for changes in the perspective; and instructions for presenting the AR display to the user.

The physiological object may be a cranium.

The first neural network may comprise a 3D U-NET. The 3D U-NET may comprise a convolutional neural network, an encoder and a decoder. The encoder may comprise a plurality of layers of convolutions, with max pooling every two convolution layers. The decoder may comprise a plurality of layers of convolutions with up-convolutions or transpose convolutions every two convolution layers. The 3D U-NET may further comprise skip connections, which transfer a convoluted image to the equally sized layers across a U-structure, skipping a portion of the encoder and decoder.

The second neural network may comprise a Reverse Edge Attention network (RE-NET). The RE-Net may comprise skip connections, with a Reverse Edge Attention Module (REAM) embedded in each skip connection.

The AR display may be generated by recognizing at least one physical marker of the physiologic object, superimposing the segmented tumor and the segmented vasculature on the captured images.

The AR display may be updated in realtime.

The AR system may further comprise a positional or inertial sensor configured to determine a positional or inertial relationship between physiological object and the user.

The AR system may further comprise a haptic output configured to produce proprioceptive stimulation according to a boundary condition.

The image of the tumor may comprise a magnetic resonance image. The angiogram may comprise a magnetic resonance angiogram.

It is also an object to provide an augmented reality method, comprising: storing 3D medical scans comprising a tumor image and an angiogram; capturing images of a physiological object from a perspective; implementing a first neural network trained to automatically segment the tumor; implementing a second neural network to segment vasculature in proximity to the tumor; implementing a third neural network to recognize a physiological object in the captured images; defining depth coded layers having opacity; generating an augmented reality display of the physiological object, tumor and vasculature based on the captured images, the segmented tumor and the segmented vasculature, dependent on the depth coded layers having opacity and dynamic changes in the perspective; and presenting the augmented reality display to the user It is a further object to provide an augmented reality system, comprising: a memory configured to store at least one type of medical image of an anatomical region; at least one camera configured to capture images of anatomy from a dynamically changing perspective; at least one processor configured to: receive the images of the at least one type of medical image; receive the captured images; implement at least one segmenting neural network trained to automatically segment the at least one type of medical image; implement an object recognition neural network trained to recognize the anatomical region in the captured images; and generate an augmented reality representation of the at least one type of medical image merged with the anatomical region from the dynamically changing perspective; and an output port configured to present the augmented reality representation.

The at least one type of medical image may comprise a 3D angiogram type of medical image and a 3D tumor type of medical image.

The at least one segmenting neural network may comprise a first segmenting neural network configured to distinguish vascular tissue from nonvascular tissue, and a second segmenting neural network configured to distinguish tumor tissue from nontumor tissue.

The at least one processor may be further configured to visualize an internal region of the anatomy.

The anatomical region may be the cranium. The least one type of medical image may comprise a first type of medical image selected from the group consisting of at least one of a magnetic resonance angiogram and a computed tomography angiogram, and a second type of medical image comprising a magnetic resonance image.

The at least one segmenting neural network may comprise a 3D U-NET, having at least a convolutional neural network, an encoder and a decoder. The encoder may comprise a plurality of layers of convolutions, with max pooling over multiple convolution layers, and the decoder comprises a plurality of layers of convolutions with up-convolutions or transpose convolutions over multiple convolution layers.

The 3D U-NET may further comprise skip connections, which transfer a convoluted image to the equally sized layers across a U-structure, skipping a portion of the encoder and decoder.

The object recognition neural network may comprise a Reverse Edge Attention network (RE-NET) with skip connections, with a Reverse Edge Attention Module (REAM) embedded in each skip connection.

The augmented reality representation may be generated by recognizing at least one physical marker of the anatomical region, and superimposing the segmented at least one type of medical image on the captured images.

The augmented reality representation may be updated in realtime.

The augmented reality representation may comprise a haptic output configured to produce proprioceptive stimulation corresponding to a boundary condition.

It is a still further object to provide an augmented reality system, comprising: a memory configured to store data from volumetric medical images comprising a plurality of image types of characteristics of an anatomical region; an augmented reality user interface comprising at least one camera, at least one inertial sensor, and a display configured to overlay a computer generated image on a live action image; at least one automated processor, configured to: determine a viewport of the augmented reality user interface; recognize an orientation of an anatomical region in the viewport in realtime using a convolutional neural network; overlay a representation of the stored data on the viewport; and control the augmented reality user interface.

The volumetric medical images may comprise a 3D angiogram, and the segmented representation of the stored data may comprise a fusion of the plurality of image types.

The at least one automated processor may be further configured to segment the volumetric medical images using at least one neural network, and to overlay the segmented volumetric medical image on the viewport.

The volumetric medical images may further comprise a magnetic resonance image of a brain tumor, and the at least one automated processor is further configured to segment the 3D angiogram, segment the magnetic resonance image of a brain tumor, label elements as foreground and background, and to apply obscuring logic based on relative depth.

The at least one automated processor may be further configured to segment the 3D angiogram and segment the magnetic resonance image of the brain tumor with a 3D U-NET, having at least a convolutional neural network, an encoder with max pooling and a decoder with up-convolutions or transpose convolutions, wherein the 3D U-NET further comprises skip connections, which transfer a convoluted image to the equally sized layers across a U-structure, skipping a portion of the encoder and decoder.

The object recognition neural network may comprise a Reverse Edge Attention network (RE-NET) with skip connections, having a Reverse Edge Attention Module (REAM) embedded in each skip connection.

The at least one automated processor may be further configured to recognize at least one physical marker of the anatomical region, and superimpose the segmented at least one type of medical image on the captured images.

DETAILED DESCRIPTION OF THE PREFERRED EMBODIMENTS

Example

"BRATS_001.nii.gz" was imported from both the image and label folders from the BraTS2020 Dataset into a MATLAB project. The MATLAB nifitread( ) function was used to load the data. The RGB value (255, 0, 0) was passed in as a colormap argument for volshow(to change the label to a different color and the alpha value 100 was passed into the alphamap argument of the full model to make it partially transparent so the tumor can easily be seen. After finishing the code, the MATLAB program was run using the green "Run" button at the top, and an interactive window opened with a 3D viewer displaying the full brain as well as the highlighted tumor (see Appendix A).

To construct the AI model that was able to outline, or segment, the brain tumor in each slice comprising the 3D model, Google Colab was opened in a web browser and a new notebook was created. The runtime of the notebook was set to GPU (Graphical Processing Unit) by clicking the Runtime dropdown, allowing access to a powerful GPU across the cloud.

The pre-installed Python libraries (cv2, glob, PIL, numpy, pandas, seaborn, matplotlib, keras, sklearn, and tensorflow) were imported into the notebook (see Appendix B). The libraries nilearn and nibabel were also installed.

Brain Tumor Segmentation

The composition of the brain tumor segmentation deep learning model is detailed through the following processes.

Figure 1:
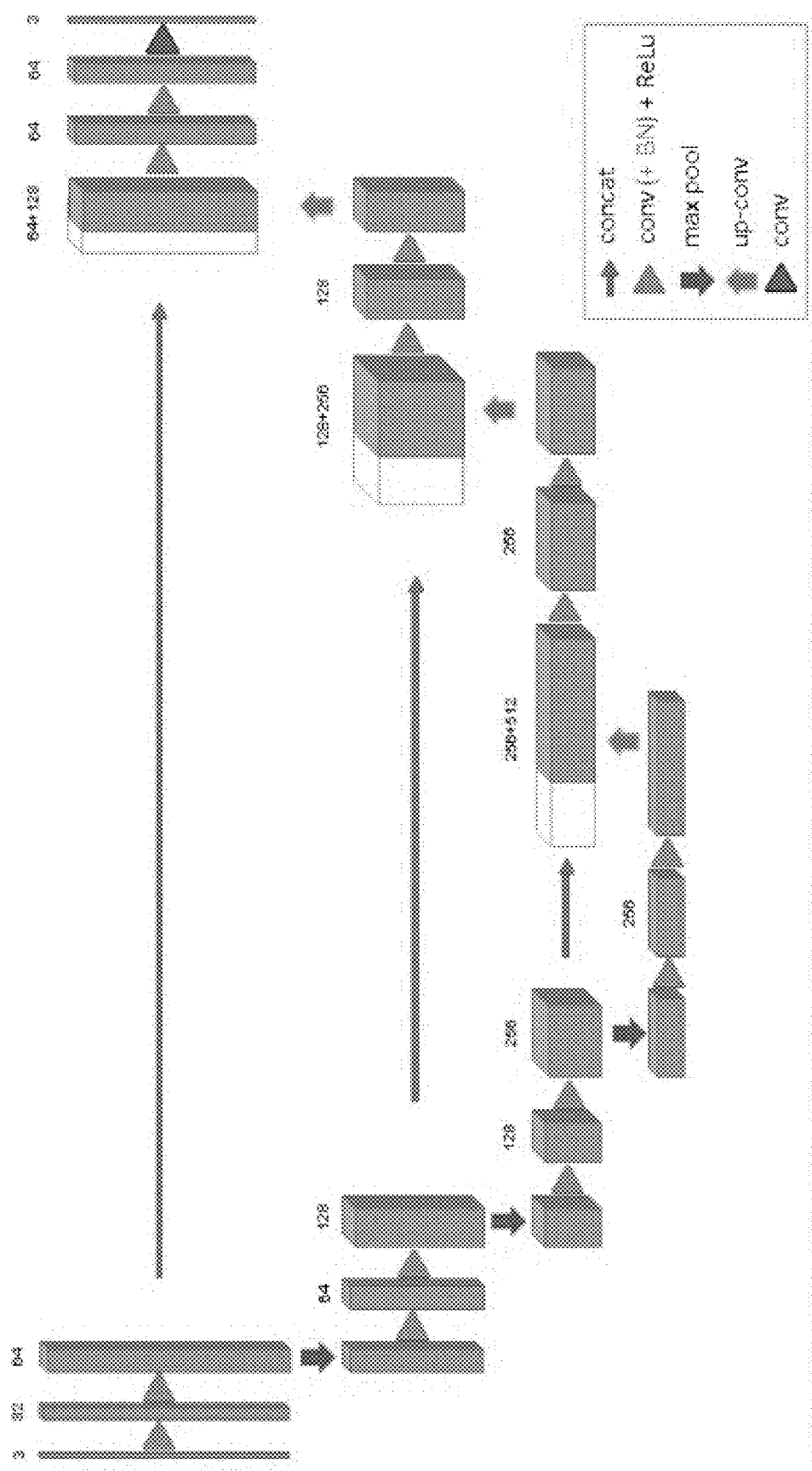
FIG. 1 shows a schematic representation of the RE-NET structure.

The classes were defined using a dictionary; 0 is "not tumor", 1 is "necrotic core", 2 is "edema", and 3 is "enhancing". Each pixel of the images in the .nii files is already labeled with one of these values. The data was displayed in slices by loading a test .nii file from the BraTS Dataset with nibabel.load( ) and displaying the file with plt.imshow( ) as shown in FIG. 1. All slices of the data were also displayed at once, shown in FIGS. 2A and 2B, to visualize in which slices was the brain placed, and which slices could be spliced off to reduce memory (see Appendix C).

The U-Net is the algorithm that seeks to predict the borders of the tumor. The U-Net algorithm was constructed in Keras, using a series of Convolutions, Max-Pooling, and Up-convolutions to alter the image so it is easier for the computer to process. Firstly, two convolutions were added to the input using Keras conv2( ) method and then a Max Pooling layer with Keras MaxPooling2D( ). This process was repeated three more times. Then, two convolutions and an up-convolution were added with the Keras method conv3DTranspose( ).

This process was repeated three more times. Finally, three convolutions were added to output the segmentation map. Appendix D shows the code for the algorithm.

The accuracy of the model was tested using the DICE (Diverse Counterfactual Explanation) coefficient, which returns a value depending on how much the prediction overlaps with the real outline, or the ground truth. A function called DiceCoefficient( ) was created, and it took in two arguments, truth and prediction (see Appendix E).

Keras.flatten( ) was called on both truth and prediction, and then the two were multiplied to find the intersection of truth and prediction. The following code shows this:

The value of two times the pixels in the intersection divided by the sum of the pixels in both truth and prediction were returned using 2×len(intersection)/(len(truth)+len(prediction)).

The entire BraTS Dataset was then split into three parts: 70% train, 15% validation, and 15% test (see Appendix F).

The training data, validation data, and test data sets were loaded in small batches using Keras DataGenerator. The DataGenerator( ) function was called on each of the train, validation, and test IDs (see Appendix G).

The model was trained with model.fit( ), passing the training data, 35 epochs (number of cycles), and validation data as arguments.

A file was loaded in from the test dataset using nibabel.load(and the AI model was run on it with model.predict( ). Matplotlib was used to display the prediction, with plt.imshow( ) (see Appendix H and Appendix I).

All the images from the segmented file were gathered into a NumPy array with np.array( ) and it was converted into a .nii file with nibabel.NiftiImage( ). The file was then saved on the computer as a .nii file.

Cerebrovascular Segmentation

Cerebral vasculature was generated from MRA through deep learning to be visualized in AR along with the brain and tumor. The dataset, TubeTK 100 healthy MRAs, was first downloaded from Kitware Medical datasets. The MRA training data had to be converted from the .mha file format to the .nii file format in order to be fed into the algorithm, so several helper scripts were programmed to automatically iterate through the folders and convert files using the SimpleITK library. The 42 labels (3D binary models of the vasculature), stored in .tre file format, also had to be converted into .nii files. A helper script was used to convert them into a .vtp poly data file, and then each one was manually inputted into the Slicer software, along with its respective .mha file. Each file was converted into a segmentation, resized to the correct dimensions according to the respective .mha file, and then exported as a .nii file.

The folders were rearranged and uploaded to Google Drive, so that the training folder contained 32 images and labels, and the test folder contained 10 images and labels. The rest of the MRAs were put in an unlabeled folder.

A new Google Colab notebook was opened and the runtime type was changed to Premium GPU. The necessary libraries were imported and installed and Google Drive was mounted (see Appendix J). To ensure the images and labels were generated correctly a function was written and called to visualize slices of the data.

The Visdom framework, a library developed by Meta, was used to collect, monitor, and plot several segmentation metrics as the model was training. The server was set up on a local tunnel and was kept on for the duration of the training. A plotter object was created with methods to create graphs of seven segmentation metrics: loss, accuracy, sensitivity, specificity, intersection over union (IoU), DICE coefficient, precision, and area under curve (AUC) (see Appendix K).

Figures 2A, 2B:
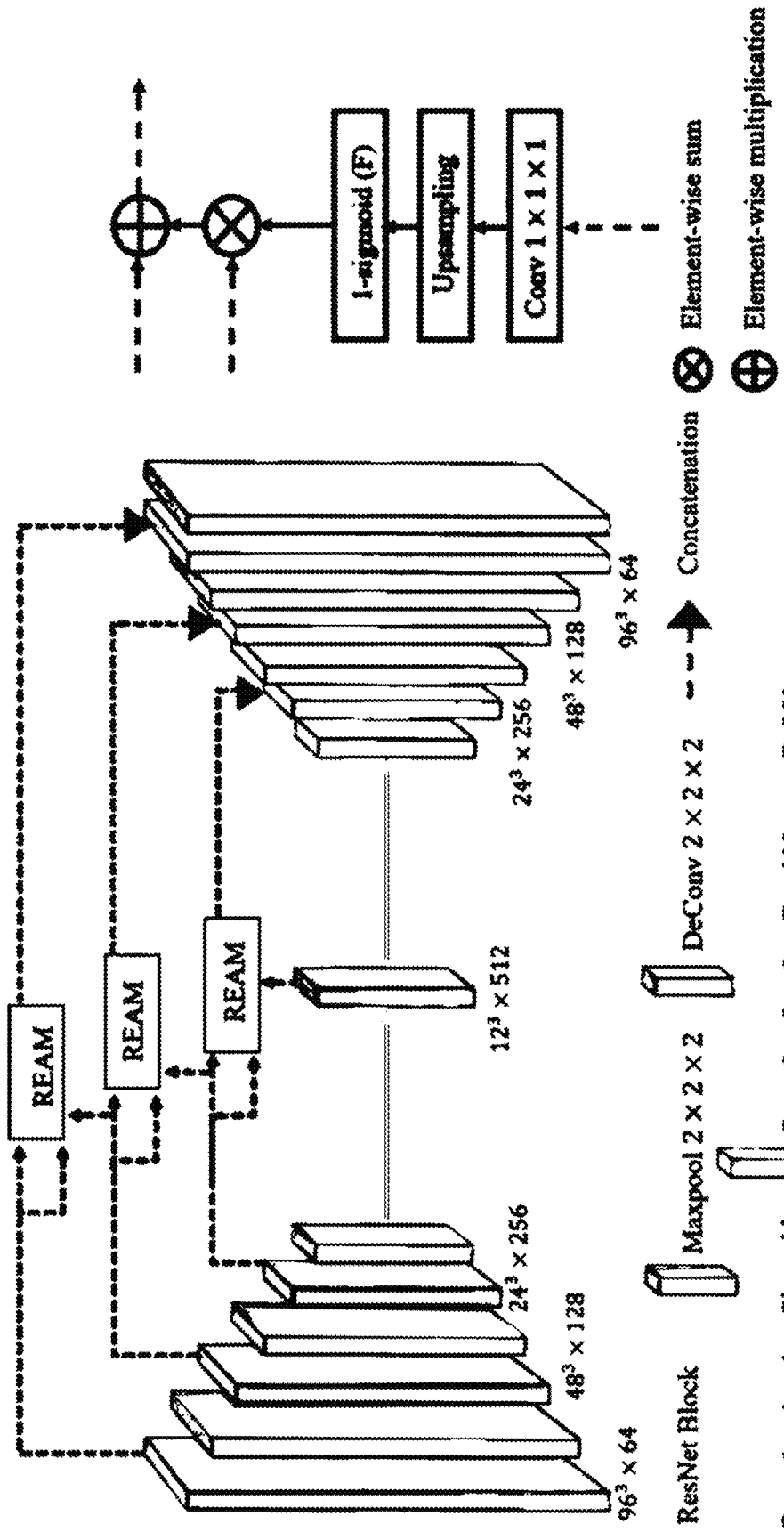
FIGS. 2A and 2B show a schematic representation of the RE-NET structure and REAM

A specialized deep learning algorithm, known as an RE Net (Reverse Edge Attention Network) was implemented for cerebrovascular segmentation; the algorithm structure is shown in FIGS. 2A and 2B (From "Cerebrovascular Segmentation in MRA via Reverse Edge Attention Network," by H. Zhang, L. Xia, J. Yang, H. Hao, J. Liu, Y. Zhao, 2020, *MICCAI*2020, 12266(1), p. 66-75 (doi.org/10.1007/978-3-030-59725-2_7)).and the program is in Appendix L.

This algorithm featured a series of convolution and max pooling layers followed by a series of convolutions, batch normalizations, and deconvolutions. A form of data augmentation known as Random Patch Crop was also programmed to increase the variability of training data and therefore the overall accuracy of the model. Arrays of size 96×96×96 voxels were randomly selected to be removed from a training sample (see Appendix M).

A data loader function was also written to prepare the data to be loaded into the model during training. It first fetches the file paths into an array and then loads each file into a Numpy array from the Nifti file format using NiBabel functionality.

A metrics function was written to calculate the several metrics listed above using the true positives, true negatives, false positives, and false negatives. This function is called during evaluation in training (see Appendix N).

Several training values were then defined in a dictionary such as learning rate and number of epochs. Functions were written to adjust the learning rate of the model and save the model as a .pkl file at certain intervals or whenever it achieved the highest DICE Coefficient.

The model was then trained on an Nvidia Tesla T4 GPU through Google Colab and used a parallel computing platform known as CUDA for faster training. As the model was trained, the evaluation metrics for each epoch were plotted through Visdom (see Appendix O).

After the model was trained, an MRA from the same patient whose MRI was segmented by the brain tumor segmentation model was loaded as a numpy array. The model with the best DICE coefficient was run on the array and it output a binary mask (see Appendix P). This was then saved as a .nii file and verified in Slicer compared to the ground truth to verify the prediction was accurate. The neurolabusc/nii2mesh github repository was again used to convert the cerebral vasculature into a .obj file to be visualized.

White Matter Tractography

White matter tractography is a three-dimensional modeling technique employed for the visualization of nerve tracts obtained through diffusion MRI. These models play an important role in neurosurgical contexts, particularly in the removal of brain tumors, as they aid in preserving functional connectivity around eloquent neurological structures and essential nerve pathways. Furthermore, a patient-specific white matter tractogram significantly enhances surgical planning by providing insights into potential obstructions, thereby minimizing the risk of neurological damage. (See Appendix Q).

The creation of a patient-specific white matter tractogram involves the application of several algorithms, facilitating the transition from medical scan data to AR visualization. At each voxel instance of the diffusion MRI, water diffusion is recorded, encompassing both direction and magnitude measurements. The DMDG algorithm is employed to generate multiple modalities of tractography, extracting optimal information. Eigenvalues and eigenvectors corresponding to each diffusion tensor at every voxel are computed to convert the diffusion MRI into an operable format. The fractional anisotropy, a quantifiable metric of the degree of diffusion, is calculated for every diffusion tensor. White matter tracts, characterized by anisotropic diffusion influenced by the myelin sheath barrier, exhibit higher fractional anisotropy values in contrast to lower values indicative of isotropic diffusion.

Seed points, selected through a uniform predefined procedure referencing anatomical landmarks, play a pivotal role as starting points for the trajectory mapping undertaken by the DMDG. This mapping follows the most probable pathway within predefined constraints, such as the region of interest. The outcome is a bundle of streamlines representing the white matter tractogram, formatted in a vector-based structure compatible with widely used 3D visualization software.

For the streamlines to be visualized in AR, they must have volume, resulting in the creation of tubes characterized by three edges and vertices at 15-degree or greater angle changes along the streamlines. This optimization is necessary for enhancing model performance in the AR environment.

These processes yield patient-specific models, the corpus callosum tractogram and the full connectome tractogram. By leveraging white matter tractography, the system advances surgical planning and contributes to a comprehensive understanding of neurological structures within an AR context.

To simulate the brain, tumor, and cerebral vasculature being superimposed during training or live surgery, a head was 3D printed for the models to be displayed inside of through AR. To accomplish this, a head model was first designed in Fusion 360, and cutouts were made for colored blocks to be inserted to increase features and improve detection since the head is relatively uniform and featureless.

The head model was exported as a .obj file and imported into the Vuforia Model Target Generator. The Model Target Generator used Advanced Model Generation and trained a deep learning model using data from the head CAD so it would be able to recognize the head from all angles and superimpose 3D models on top of it with a greater degree of positional accuracy. After the model was trained, it was exported as a Unity Package.

Figure 3:
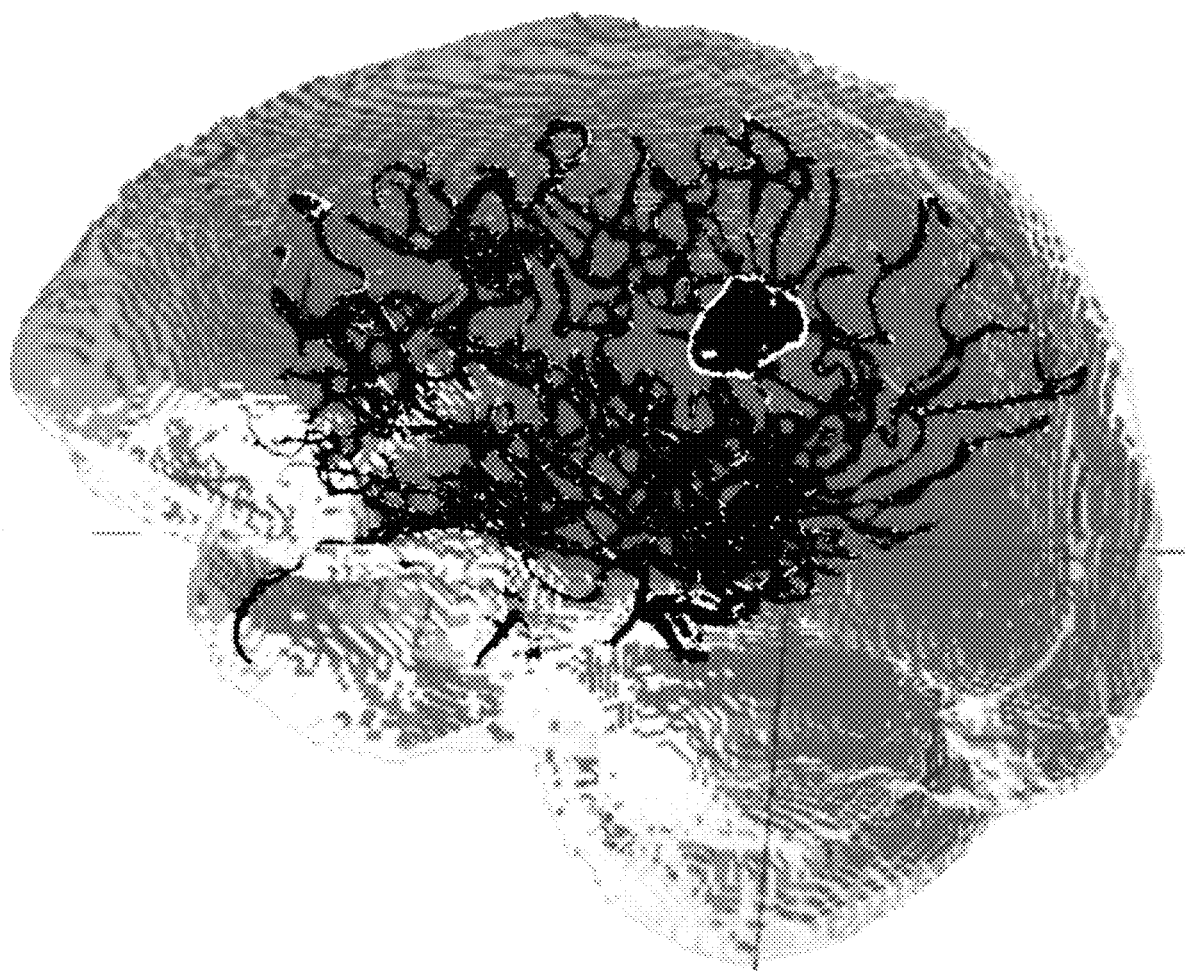
FIG. 3 shows a visualization of brain, tumor, and cerebral vasculature rendered in Unity.
Figure 4:
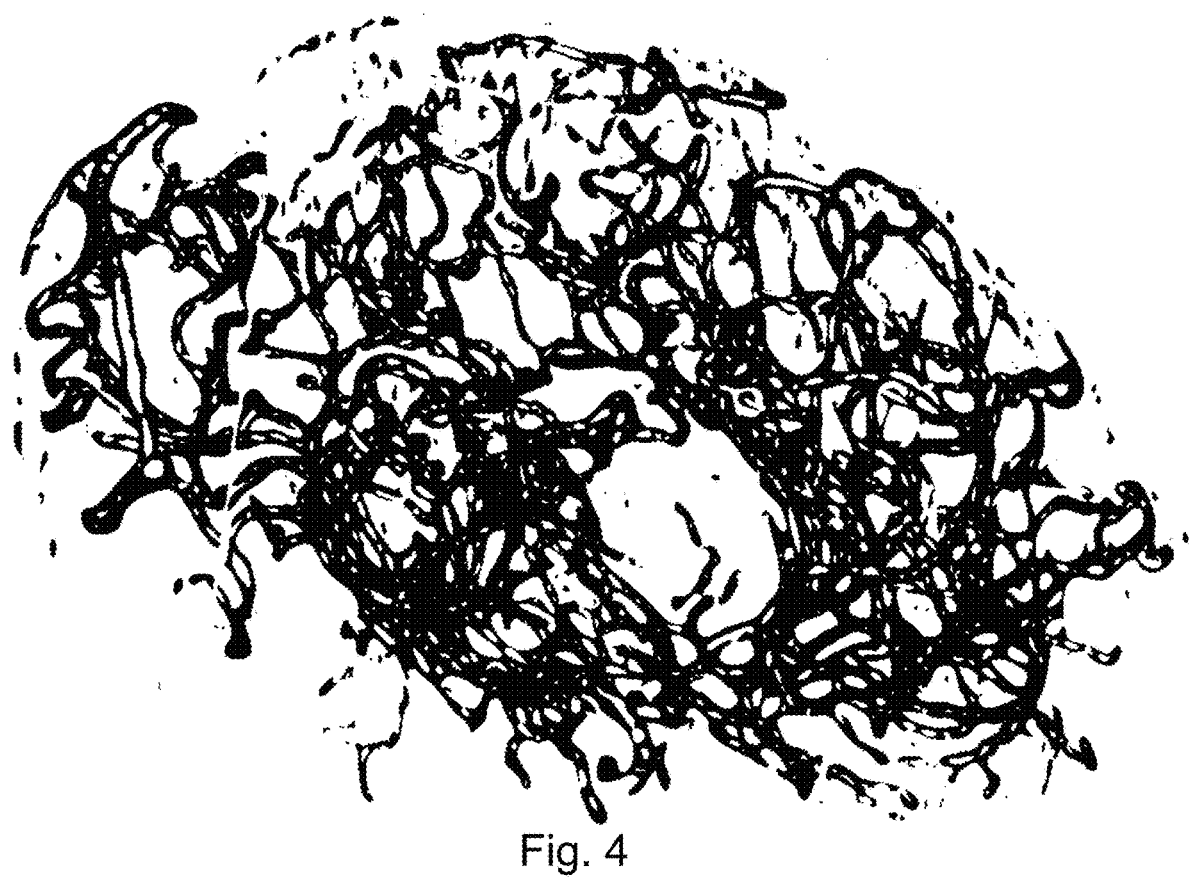
FIG. 4 shows a visualization of cerebral vasculature rendered in 3D Slicer.

A new Unity project was then created with Android Build Support installed, and Vuforia was added to the project. From the Vuforia menu, an AR Camera was added, and the ARCore requirement in its settings was set to "Optional". The Unity Package was then dragged into the scene, and in the AR Camera settings, it was set as the main database. The 3D head model is now in the scene. The brain, tumor, and cerebral vasculature were then dragged in, and their transforms reset and aligned with the 3D head model, so they are positioned inside it. Different materials were created, and their colors, transparency, and emission were adjusted and applied to each of the 3D models for clearer visualization as shown in FIGS. 3 and 4.

Transferring Models

An apparatus was essential to enable the seamless transfer of medical scans and 3D models to the application deployed on the Hololens device. This procedural aspect was optimized through the utilization of the Unity Game Engine, enabling the deployment of both the 3D models and the application to the head-mounted display device. The brain tumor Magnetic Resonance Imaging (MRI) dataset and the Diffusion Tensor Imaging (DTI) dataset stored the scans in the Neuroimaging Informatics Technology Initiative (NIfTI) file format. The file format initiates with a header section conveying essential details about the scan, including voxel size and orientation information. Each voxel's value is preserved in a 3D array, with each value represented as a floating-point number. For the purpose of training and evaluating the deep learning models, the NIfTI files underwent conversion to NumPy arrays, facilitating efficient processing. In the case of tumor segmentations, the NumPy arrays were subsequently reconverted into compressed NIfTI files to mitigate memory usage. DTI segmentations were stored in the Visualization Toolkit (VTK) format as fiber bundles or streamlines, without volume representation.

The dataset for cerebral vasculature was initially provided in VTK format and underwent conversion to NIfTI using 3D Slicer, following the same protocol as the tumor scans, before being uploaded to the deep learning system. The resultant vasculature segmentations were preserved in the NIfTI file format. The 3D Slicer application played a pivotal role in standardizing file formats for AR utilization: the tumor and vasculature NIfTI files were retrieved as Filmbox (FBX) files. Tractograms underwent an initial volumization process, generating tubes characterized by 3 edges and vertices at 15-degree or greater angle changes to enhance model performance in the AR environment. Subsequently, these tubular tractograms were likewise saved as FBX files. The 3D Slicer application also assisted with the uniform resizing of the anatomical models to a standardized scale, defined by the original tumor MRI. In the FBX format, all anatomical models were aligned to the same scale and orientation. These standardized anatomical models were uploaded into the Unity application for further customization of visualization parameters.

AR Surgical Aid Application

Through the Unity Game Engine and the Mixed Reality Toolkit, an application for Universal Windows Platform was constructed and deployed to the head-mounted display device, the Microsoft Hololens 2. The application possesses several functions and features to provide a comprehensive and easy-to-use surgical aid for brain tumor removal. The tumor, vasculature, and tractograms are uploaded to the application on the head-mounted display device. In the main functionality of the surgical aid, these models appear as holograms superimposed onto the patient head with significant accuracy.

Hololens Spatial Mapping

The head-mounted display device incorporates several sensors utilized to mitigate any perceptible jitter in airborne holograms lacking specific anchors. The foundation of the Hololens' spatial awareness lies in Simultaneous Localization and Mapping (SLAM), wherein salient environmental features are tracked during device movement. Upon application initiation, the display device scans the user's surroundings, creating a geometric reconstruction and fashioning a 3D mesh through sensor data. This mesh encompasses surfaces like walls, floors, objects, and various spatial features. Notably, this mapping system is dynamically adaptive, delivering real-time updates to accommodate alterations in object positions or shifts in the user's environmental context.

Spatial anchors emerge as a pivotal facet of Hololens functionality, expanding on the spatial mapping system's data. These anchors can tether holograms and virtual elements to any point within the 3D map. As the user traverses the environment, holograms anchored through spatial points persist in their perceived locations, a device integrated into the surgical application's management of expanded models, nervous mapping modalities, and medical scan modalities. While the spatial anchor system fortifies the surgical aid's precision in the main purpose of superimposing anatomical models on the patient's head, it proves insufficient for the exactness mandated by neurosurgical procedures. Thus, the tracking algorithm for retroreflective markers becomes imperative.

Ensuring the holograms' steadfastness during the head-mounted display device's motion and facilitating their manipulation according to the surgeon's needs is imperative for the seamless functioning of the application.

Tracking Algorithm Retroreflective Markers

The system purposed for precise tracking of the patient's head position in a surgical environment was devised to ensure recognition by the head-mounted display when specific markers affixed to the patient's head come into view. These markers, necessary for the tracking system, exhibit a spherical retroreflective design, causing emitted light rays to reflect back in the same direction toward the source. The experimental apparatus employs the Hololens 2 as the head-mounted display, a device with individual sensor capabilities accessible through its research mode functionality. (See Appendix R.)

Four environmental cameras contribute to the system's output: a near Time of Flight sensor (ToF), a long ToF sensor, and two RGB front cameras. The tracking algorithm developed for this system harnesses the two output frames of the near ToF sensor-short throw reflectivity (str) and short throw depth (std). The fusion of these frames facilitates the creation of a three-dimensional reconstruction of the retroreflective markers.

The operational flow initiates with a request for two frames from the near ToF depth sensor, converted into operable two-dimensional arrays. Leveraging the unique properties of retroreflective markers, they manifest as especially bright in the str stream, given the reflected light towards the sensor. However, to ensure precision, bright spots such as camera lenses and metallic surfaces are excluded through the implementation of thresholding and blob detection.

First, the str frame is normalized such that zero represents no reflectivity and one represents maximum reflectivity. The ideal threshold determined through consistent observation of the value returned by retroreflective markers from any orientation was set at 0.95. This threshold was used to binarize the array such that values below the threshold were set to zero and values above the threshold were set to one. Clusters are identified through a blob detection algorithm, accompanied by a test for similar sizes. Pixel radius measurements aid in determining the presence of clusters with similar radii, while unusually small lone clusters, potentially indicative of camera lens interference, are filtered out. The remaining clusters undergo a circularity test through the isoperimetric quotient.

In instances of marker overlap from a specific orientation, clusters are omitted, given that reconstruction remains achievable from the remaining markers. The centers of the remaining circular blobs are recorded and stored in a sparse matrix purposed to minimize memory usage. These recorded centers are subsequently mapped to the output frame std, facilitating the creation of a comprehensive 3D reconstruction of the marker elements. Pixel-to-coordinate translation in 3D space occurs for the std stream, with actual distance metrics between markers and the camera considered unnecessary, as superimposition remains proportionate to inter-marker distances.

The centroid of the markers serves as the pivotal point for superimposing anatomical models. The number of pixels in the interpolated frames between markers becomes the basis for measurement and is used to calculate the centroid. The orientation of the models superimposed on the centroid is determined from any camera position viewing the markers. To achieve this, a pose estimation algorithm is implemented, identifying translation and rotation. The centroid is converted to a translation vector relative to the camera, and using the Perspective-n-Point pose estimation algorithm, a rotation matrix is derived from the 3D positions of the markers and the thresholded str stream. Anatomical models are then superimposed based on the translation vector and rotation matrix, augmented by a constant scale and additional translation to account for the cameras' offsets in calibration.

Model Visualization

As dictated by the specified tracking algorithm, the anatomical models employed for precise superimposition onto the patient's head-comprising the tumor, vasculature, and major white matter tracts—utilize a defined visualization process for rendering in AR. In real-time, these models are virtually positioned onto the patient's head and tracked utilizing a distinctive set of retroreflective markers preprogrammed for recognition by the head-mounted display device.

The anatomical models dynamically adhere to the movement of the retroreflective markers, employing spatial mapping capabilities to retain their positions in scenarios where marker occlusion occurs. This responsive tracking mechanism ensures the seamless alignment of anatomical models with any potential shifts in the patient's head position during the surgical procedure.

To enhance visual clarity and prioritize critical information, each anatomical model is assigned distinct textures characterized by varying colors and transparencies. This design choice ensures optimal visibility of the tumor, followed by the vasculature and white matter tractogram in descending order of importance. Such hierarchical visualization aids surgical precision and eliminates occlusion of important anatomy.

The application possesses a graphical user interface, providing an intuitive and unobtrusive means for the surgeon to selectively occlude any of the anatomical models based on surgical requirements. This functionality enables the surgeon to tailor the visual representation according to specific needs, enhancing the adaptability of the AR system to diverse surgical scenarios. The graphical user interface integrates into the surgeon's workflow, fostering a user-friendly and efficient operative environment.

User Interface

A user-friendly graphical interface, specifically tailored for seamless operation during surgical procedures, is implemented in the application. Leveraging the capabilities inherent in the head-mounted display device, including handlers, solvers, and hand tracking, a haptic-based button panel has been integrated. This panel dynamically aligns with the field of view of the head-mounted display while maintaining its peripheral position in the lower left quadrant of the visualization. This button panel is equipped with 3D colliders, and senses finger contact with the virtual button using hand tracking. The user interface can be interacted with as if it were physical, mimicking standard procedure and maximizing ease of use.

The graphical user interface exhibits responsive feedback, through subtle movements upon activation and color alterations indicative of toggled states. The multifaceted capabilities of the button panel extend to the ability to deactivate any actively superimposed anatomical models on the patient's head. Furthermore, it serves as the conduit through which the three distinctive modes of the surgical aid are initiated.

Surgical Aid Modes

Default Mode—Patient Head Tracking & Superimposition

This is the default mode for the application.

Mode 1—Expanded Models

Mode 1 entails the enlargement of anatomical models to a scale of the user's preference, detaching these models from the constraints of the patient's head size. This enlargement is particularly advantageous for preoperative planning and analysis, enabling a more detailed examination of visual intricacies.

Mode 2—Nervous Mapping

Mode 2 is an AR implementation of the neurosurgical procedure known as Intraoperative Neurophysiological Monitoring (IONM). Functional mapping of the nerves within the brain is vital to understanding patient responses when dealing with tumors near critical areas of brain function, especially subcortical pathways. Utilizing patient-specific Diffusion Tensor Imaging (DTI), the various tractograms are visualized in a dynamic interface for a comprehensive understanding of nervous mapping. These visualizations—the white matter tractogram and full connectome—can be selectively shown through the usage of the button panel. The white matter tractogram is colored using fiber orientation color coding, such that the primary diffusion direction is reflective of a certain color. The x-axis increases with the red value, the y-axis with the green, and the z-axis with blue in an RGB color space, allowing fiber direction to be delineated. The connectome is rendered in color according to which nervous structures correspond to which brain function including the networks for motor control, sensory processing, language processing, and higher-order capabilities such as cognition, emotion, and conation Mode 3—Medical Scan Viewer Mode 3 facilitates the visualization of medical scans in three dimensions during surgery, eliminating the need for the user to switch between the surgical site and external 2-dimensional screens. This AR presentation maintains visual consistency with external screens, yet it unfolds in real-world space. Compatible scans, including but not limited to MRI, MRA, computed tomography (CT), and DTI, can be visualized using two distinct methods: the rendering of a single pivotal slice or the uploading of a 3D medical scan, or the rendering of any slice through a slider interface situated in the lower left corner of the visualization.

Hand and Eye Tracking

The head-mounted display device possesses functionality for tracking the user's hand and eye movements to facilitate natural and seamless interaction with holograms and other virtual elements. Hand tracking is done through a workflow involving the stereoscopic cameras recognizing the hands paired with the short-throw depth sensor identifying the pose of the hand. This pose is utilized to calculate the gestures of the hand: tapping, grabbing, pinching, and swiping that correlate with a specific functionality. These gestures allow users to navigate the features of the application, including interacting with the surgical holograms and utilizing the button panel to switch modes, intuitively and unobtrusively.

The eye tracking functions through user-specific calibration ensuring properly fitted visualizations. The surgical aid especially utilizes this function through hands-free processes, allowing solely gaze and voice to control the application. For example, the buttons in the panel can be toggled through the user gazing at them and orating the voice command, useful in circumstances of surgery where both hands are needed in the surgical site.

Solvers and Handlers

The concept of solvers and handlers extends the functionalities of the hand and eye-tracking capabilities inherent in the head-mounted display device. These systems serve as the controllers of movement for virtual elements anchored to specific points or objects in space, encompassing a spectrum that includes, but is not limited to, user interface elements, medical scans, and expanded anatomical models.

The paramount objective of solvers and handlers is to synchronize the movement of virtual models with the user's line of sight, providing a natural and three-dimensional perceptual experience. This synchronization is achieved without rigidly tethering the virtual elements to the screen, thereby preserving a dynamic and immersive visual interaction. For instance, the movement of user interface elements is subject to specific constraints, necessitating a predetermined distance from the user and positioning in the bottom left of the view.

However, as the user's gaze turns, the UI remains in the same position in real space until an angle of five degrees rotation is achieved; at this moment the UI elements begin turning with the user. This dead zone of movement at the initial moments of rotation builds the 3D appearance of UI. This deliberate design choice contributes to a more realistic and immersive visual experience by mitigating abrupt shifts during gaze transitions.

Furthermore, the solver and handling system is engineered to facilitate the manipulation of virtual objects in a realistic manner. In the case of user interface elements, the system computes the position and gestures of the hand, determining whether a button is toggled. This interactive capability extends to various virtual elements within the surgical application, encompassing expanded anatomical models, nervous mapping models, and medical scan volumes. Users are able to organize these elements according to their specific needs through intuitive gesture recognition, such as pinching to "pick up" a virtual model and dragging it to a different location within the surgical environment.

The versatility of this system is exemplified by the fused capabilities of solvers and handlers, allowing virtual elements to be positioned anywhere within the surgical environment. These elements consistently maintain a certain distance from the user, whether suspended in midair or placed on a surface, leveraging the spatial map generated by the head-mounted display device to navigate and integrate with the surrounding environment.

Results

Two deep learning models were programmed, trained, and evaluated: one for the 3D segmentation of brain tumors, and the other for the 3D segmentation of cerebral vasculature. Both of these models were evaluated with several benchmark metrics, specifically designed for medical segmentation, derived from four values: true positives, true negatives, false positives, and false negatives. To calculate these values, the model prediction, or what the algorithm believes to be the segmentation, is compared with the ground truth, which is the segmentation that is manually done by an expert, and what the prediction should closely resemble.

Several segmentation metrics were used in the evaluation of both the brain tumor and cerebrovascular segmentation models. These main metrics were accuracy, loss, DICE Coefficient, mean Intersection Over Union (IOU), sensitivity, specificity, precision, and Area Under Curve (AUC). Each of these metrics except loss is calculated from four numbers: true positives, true negatives, false positives, and false negatives. In the case of brain tumor segmentation, each voxel is assigned a value from 0-3, with zero representing that specific voxel is not a tumor, one representing that the specific voxel is a tumor core, and so on. For the ground truth, each of these voxels is assigned by an expert radiologist, so it is considered the correct label. The AI also assigns each voxel a value from zero through three depending on what it predicts for each voxel. Its prediction is then compared with the ground truth, and true/false positives and negatives are calculated. A true positive refers to one specific voxel of the entire MRI that both the AI and the expert predicted was a tumor, so a value from one through 3. A true negative is a specific voxel that both the AI and expert predicted wasn't a tumor. Both of these are correct predictions. A false positive, however, is when an AI predicts a certain voxel to be a tumor, but it actually isn't. In the same way, a false negative is when the AI predicts a certain voxel to not be a tumor, but it actually is. True/false positives and negatives are then used to calculate the metrics listed above. In general, for segmentation, DICE coefficient and mean IOU are the most commonly used metrics.

In addition to these metrics, a Receiver Operating Characteristic (ROC) curve, as well as a Precision Recall Curve, was plotted to identify optimal thresholds. The AI will return probabilities on the likelihood of each voxel being a positive, and then a threshold value, usually, is used to convert the prediction to binary. The ROC and Precision Recall curves will identify a threshold other than 0.5 that will minimize false positives and false negatives. This was done for both brain tumor and cerebrovascular segmentation. Lastly, several confusion matrices were plotted using the true/false positives and negatives. Confusion matrices are a way to visually represent the number of true/false positives and negatives, and the color is assigned based on their proportions.

The brain tumor segmentation model made predictions on three distinct classes: the tumor core/necrotic tissue, edema, and enhancing. The original MRI is overlaid on each panel, and then the classes as well as the ground truth are drawn on top of the original MRI.

Table 1 communicates the mathematical formulas for the several segmentation metrics used in this project: loss, accuracy, mean Intersection Over Union (IOU), DICE coefficient, precision, sensitivity, and specificity.

TABLE 1

| Metric | Formula | Maximized or Minimized |
|---|---|---|
| Loss | NA | Minimized |
| Accuracy | (TP + TN)/(TP + TN + FP + FN) | Maximized |
| IOU | TP/(TP + FP + FN) | Maximized |
| DICE Coefficient | (2 × TP)/(FP + FN + 2 × FP) | Maximized |
| Precision | TP/(TP + FP) | Maximized |
| Sensitivity | TP/(TP + FN) | Maximized |
| Specificity | TN/(FP + TN) | Maximized |

Segmentation Metric Formulas

Note. The Loss metric is not computed with true/false positives and negatives, it is computed with an algorithm and used to adjust the learning rate of the model.

Each metric utilizes a different interpretation of true/false positives and negatives to evaluate the model on several fronts. The DICE coefficient and the mean IOU are considered the best metrics in terms of overall model performance.

To evaluate the brain tumor segmentation model, the DICE coefficient for each class was calculated to discern which classes are best segmented by the model and which classes the model needs additional training on. Necrotic had a DICE score of 0.7472, edema had a DICE score of 0.7944, and enhancing had a DICE score of 0.7929.

Looking further into the specific true/false positives and negatives for each class, three confusion matrices were generated. These confusion matrices represent the number of voxels (3D pixel) that fall into each category, as well as the percentage of the entire MRI those voxels make up. One last test was done on the brain tumor segmentation model, and that was implementing a Receiver Operating Characteristic (ROC) curve for all classes combined, to adjust the threshold at which the prediction assigns a 1 or 0 to each voxel.

TABLE 2

|  | Necrotic | Edema | Enhanced |
| --- | --- | --- | --- |
| True Negative: | 99.899% (1637013) | 98.656% (1637013) | 99.213% (1630751) |
| False Positive: | 0.028% (477) | 0.172% (2847) | 0.026% (428) |
| False Negative | 0.028% (466) | 0.174% (2884) | 0.031% (517) |
| True Positive: | 0.042% (725) | 1.001% (16575) | 0.349% (5730) |

The ROC curve analyzes and depicts the resulting change and tradeoff of true and false positives as the threshold changes. The model's prediction is an array of probabilities, of how likely it thinks a certain voxel is part of a tumor or its surroundings. From this prediction, a threshold value of usually 0.5 is selected, and the prediction is converted into a binary array of 1s and 0s based on that threshold. The lower that threshold, the more true and false positives the model will hold, and the higher the threshold, the fewer true and false positives the model will hold. Implementing the ROC Curve allows for a suitable threshold to be found, one that maximizes the number of true positives without greatly increasing the number of false positives. The dotted diagonal line represents a random classifier, a model that has zero training and makes random predictions. The blue line represents the ROC curve of the brain tumor segmentation model; the closer the line is to the left corner, the more accurate the model is considered.

An ROC Curve was generated based on the sensitivity and specificity metrics, and the Area Under Curve (AUC) was calculated to be 0.856.

Additionally, a confusion matrix was plotted, displayed the true/false positives and negatives.
  True Negative: 99.843% (25649877)
  False Positive: 0.051% (13154)
  False Negative 0.045% (11544)
  True Positive: 0.060% (15537)

Discussion

The brain tumor segmentation model outputs similar results in terms of metrics for the train, validation, and test datasets. The DICE coefficient score was 0.69 for the brain tumor segmentation model, which implies the model is exceptionally accurate, however, some incorrect predictions are present. Taking into consideration the size of the tumor as well as the application of this project, certain slight inaccuracies, for example, pixels between the class boundaries which is where the model made most of the incorrect predictions, are negligible.

Of the three classes, necrotic, edema, and enhancing, the edema class was segmented the most accurately with a DICE score of 0.7944; the enhancing class also had a close DICE score of 0.7929. The necrotic class had a slightly lower DICE score of 0.7472 most likely due to unclear boundaries on the MRI between the edema and tumor core. The tumor is the core on the inside, the edema, which is a buildup of fluid, surrounds the tumor, and enhancing refers to the section surrounding the edema that is easily visible in a contrast-enhanced MRI due to the concentration of blood vessels. Slight gradient differences between these classes can lead to some model inaccuracies, but these are usually negligible for the purpose of this project.

As for the confusion matrices, voxels in the true negative category compromise an overwhelming percentage because the tumor is relatively small compared to the entire scale of the MRI. With the heatmap on a logarithmic scale, larger percentages are colored darker, and it can be concluded that both the true negative and positive values are much greater than the false negative and positive values. The brain tumor segmentation model has a near-perfect ROC curve, as it maximizes the Area Under the Curve (AUC) signifying an extremely accurate model.

The same metrics were used to evaluate the cerebrovascular segmentation model. The DICE coefficient score, calculated from predictions on the validation dataset, was 0.75 signifying a high degree of accuracy in prediction. An ROC Curve was also plotted for the cerebrovascular segmentation model and the AUC was calculated to be 0.856, meaning the prediction correlates well with the ground truth at a certain threshold. Analyzing the shape of the ROC curve, the threshold of 0.5 currently set to produce the binary mask from the prediction is likely to not be the most effective threshold. To find the optimal threshold, the G-mean and Precision Recall Curve were utilized. The G-mean is the square root of recall times precision, and is plotted on the ROC Curve. The Precision-Recall curve is separate graph plotted with recall/sensitivity on the x-axis and precision on the y-axis. The F or F1-score is then calculated and plotted against the curve to find the optimum threshold.

Calculating the G-mean returned an optimal threshold of 0.8953, while the F-Score returned an optimal threshold of 0.5578. Both thresholds were able to significantly reduce the amount of false positives, thus increasing the overall accuracy of the prediction.

This technology may be further enhanced to utilize locational trackers and devices to enhance the positioning and orientation of the superimposition. Rather than placing the burden solely on the prediction of the AI, actual locational arguments from the camera(s) and several nearby markers may be used to create a 3D rendering of the scene, and from there the exact position and orientation of the models can be determined.

This technology facilitates live and intraoperative craniotomy procedures and minimally invasive brain tumor resections. Surgeons can wear the AR headsets to clearly see an adjustable and comprehensive visualization of the position of the tumor, cerebral vasculature, and other data. This removes the need for the surgeon to constantly switch perspectives, between the surgical site/endoscope feed and the separate 2D screens. Additionally, the AR system removes the cognitive burden of locating the tumor through multiple perspectives, rather, it shows its location directly in the surgeon's field of view. The surgical aid can easily be adjusted to aid in other tumor removal surgeries, such as for pancreatic and colon cancers.

This system can also be used for preoperative planning, as rendering the tumor, vasculature, etc., in 3D will allow for more effective planning and collaboration. The technology may also be used in medical training, so medical students can visualize how the surgery occurs through a more interactive experience. Visualizing a tumor in 3D can allow for better communication between doctors and patients, so patients can gain a better understanding of their situation.

Figure 5:
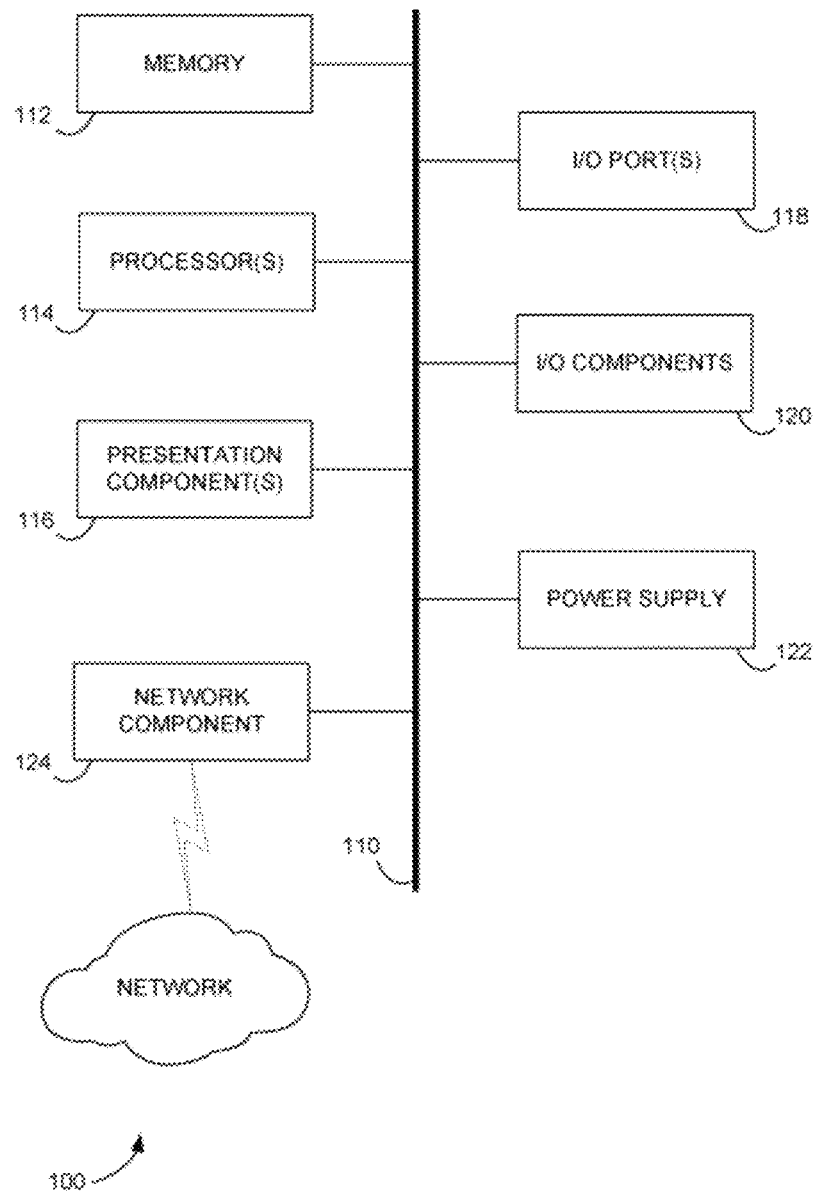
FIG. 5 shows a block diagram of an example computing environment suitable for implementing some of the various examples disclosed herein.

FIG. 5 is a block diagram from U.S. Pat. No. 10,740,966 of an example computing device 100 for implementing aspects disclosed herein and is designated generally as the computing device 100. The computing device 100 is but one example of a suitable computing environment and is not intended to suggest any limitation as to the scope of use or functionality of various embodiments of the invention. Neither should the computing device 100 be interpreted as having any dependency or requirement relating to any one or combination of components/modules illustrated.

The examples and embodiments disclosed herein may be described in the general context of computer code or machine-useable instructions, including computer-executable instructions such as program components, being executed by a computer or other machine, such as a personal data assistant or other handheld device. Generally, program components including routines, programs, objects, components, data structures, and the like, refer to code that performs particular tasks, or implement particular abstract data types. The disclosed examples can be practiced in a variety of system configurations, including personal computers, laptops, smart phones, mobile tablets, hand-held devices, consumer electronics, specialty computing devices, etc. The disclosed examples can also be practiced in distributed computing environments, such as those disclosed in FIG. 6 described in more detail below, where tasks are performed by remote-processing devices that are linked through a communications network.

The computing device 100 includes a bus 110 that directly or indirectly couples the following devices: memory 112, one or more processors 114, one or more presentation components 116, input/output (I/O) ports 118, I/O components 120, a power supply 122, and a network component 124. The computing device 100 should not be interpreted as having any dependency or requirement related to any single component or combination of components illustrated therein. While the computing device 100 is depicted as a single device, multiple computing devices 100 can work together and share the depicted device resources. For instance, the memory 112 can be distributed across multiple devices, the processor(s) 114 can be housed on different devices, and so on.

The bus 110 represents a system bus that can be any of several types of bus structures, including a memory bus or memory controller, a peripheral bus, and a local bus using any of a variety of bus architectures.

Figure 6:
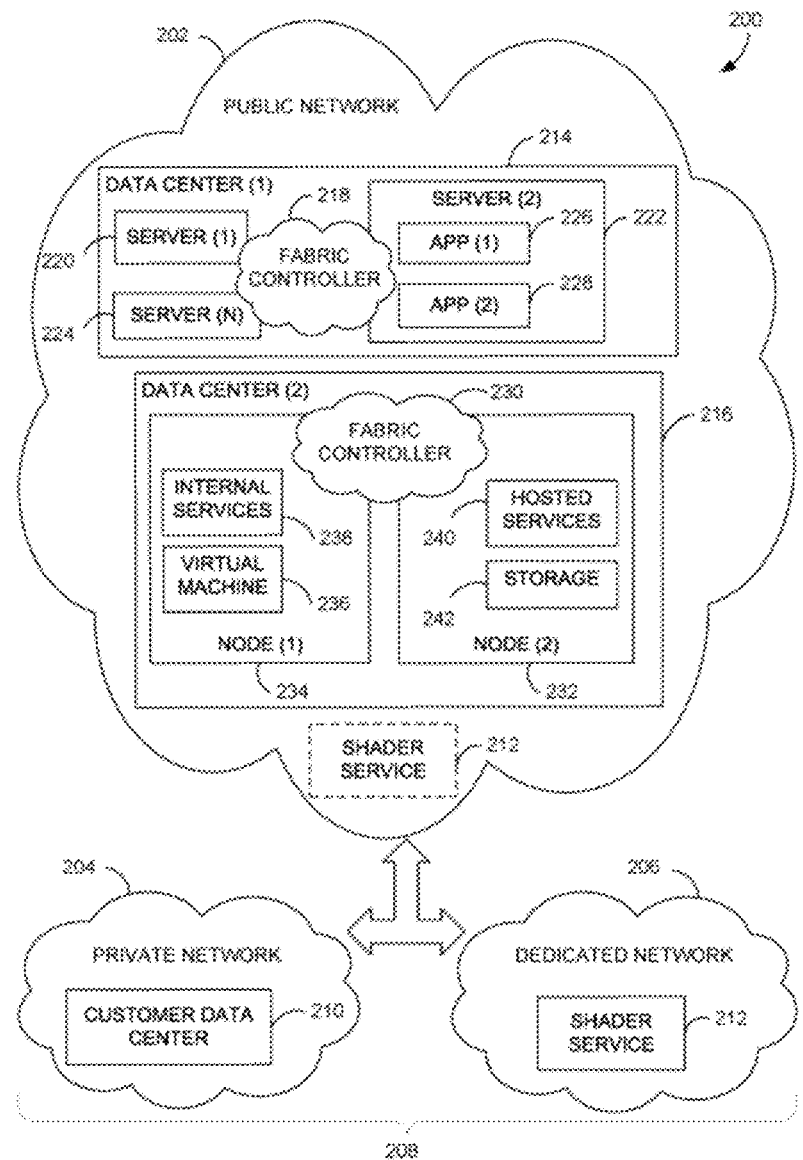
FIG. 6 is a block diagram of an example cloud-computing infrastructure suitable for a shader service implementing some of the various examples disclosed herein.

Although the various blocks of FIG. 6 are shown with lines for the sake of clarity, delineating various components is more accurately grey and fuzzy. For example, one can consider a presentation component such as a display device to be an I/O component. Also, processors have memory. Such is the nature of the art, and the diagram of FIG. 6 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 6 and the references herein to a "computing device."

The memory 112 can be used to store and access instructions configured to carry out the various operations disclosed herein. In some examples, the memory 112 includes computer-readable media in the form of volatile and/or nonvolatile memory, removable or non-removable memory, data disks in virtual environments, or a combination thereof. The memory area stores, among other data, one or more applications. The applications, when executed by the processor, operate to perform functionality on the computing device. The memory area further stores one or more computer-executable components.

Exemplary components can include a user interface component.

By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computer. Computer storage media does not, however, include propagated signals. Rather, computer storage media excludes propagated signals.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The system memory includes computer storage media in the form of volatile and/or nonvolatile memory such as read only memory (ROM) and random-access memory (RAM). A basic input/output system (BIOS), containing the basic routines that help to transfer information between elements within computer, such as during start-up, is typically stored in ROM. RAM typically contains data and/or program modules that are immediately accessible to and/or presently being operated on by a processing unit or processor.

The computer can also include other removable/non-removable, volatile/nonvolatile computer storage media, such as, for example only, a hard disk drive that reads from or writes to non-removable, nonvolatile magnetic media, a universal serial bus (USB) port that provides for reads from or writes to a removable, nonvolatile memory, and an optical disk drive that reads from or writes to a removable, nonvolatile optical disk such as a CD ROM or other optical media. Other removable/non-removable, volatile/nonvolatile computer storage media that can be used in an exemplary operating environment include, but are not limited to, magnetic tape cassettes, flash memory cards, digital versatile disks, digital video tape, solid state RAM, solid state ROM, and the like. The hard disk drive is typically connected to the system bus through a non-removable memory interface, and a USB port and optical disk drive are typically connected to the system bus by a removable memory interface.

The processor(s) 114 can include any quantity of processing units that read data from various entities, such as the memory 112 or the I/O components 120. Specifically, the processor(s) 114 are programmed to execute computer-executable instructions for implementing aspects of the disclosure. The instructions can be performed by the processor, by multiple processors within the computing device 100, or by a processor external to the computing device 100. In some examples, the processor(s) 114 are programmed to execute instructions such as those illustrated in the flowcharts discussed below and depicted in the accompanying drawings. Moreover, in some examples, the processor(s) 114 represent an implementation of analog techniques to perform the operations described herein. For example, the operations can be performed by an analog client computing device and/or a digital client computing device.

The presentation component(s) 116 present data indications to a user or other device. Exemplary presentation components include a display device, speaker, printing component, vibrating component, etc. One skilled in the art will understand and appreciate that computer data can be presented in a number of ways, such as visually in a graphical user interface (GUI), audibly through speakers, wirelessly between computing devices 100, across a wired connection, or in other ways.

The ports 118 allow the computing device 100 to be logically coupled to other devices including the I/O components 120, some of which can be built in. Examples of the I/O components 120 include, for example but without limitation, a microphone, keyboard, mouse, joystick, game pad, satellite dish, scanner, printer, wireless device, etc.

In some examples, the network component 124 includes a network interface card and/or computer-executable instructions (e.g., a driver) for operating the network interface card. Communication between the computing device 100 and other devices can occur using any protocol or mechanism over any wired or wireless connection. In some examples, the network component 124 is operable to communicate data over public, private, or hybrid (public and private) networks using a transfer protocol, between devices wirelessly using short range communication technologies (e.g., near-field communication (NFC), Bluetooth® branded communications, or the like), or a combination thereof.

A computer, or computing device, as used herein, represents any device executing instructions (e.g., as application programs, operating system functionality, or both) to implement the operations and functionality as described herein. The computing device can include a mobile computing device or any other portable device. In some examples, the mobile computing device includes a mobile telephone, laptop, tablet, computing pad, netbook, gaming device, wearable device and/or portable media player. The computing device can also include less portable devices such as desktop personal computers, kiosks, tabletop devices, industrial control devices, wireless charging stations, and electric automobile charging stations. Additionally, the computing device can represent a group of processing units or other computing devices.

Figure 7:
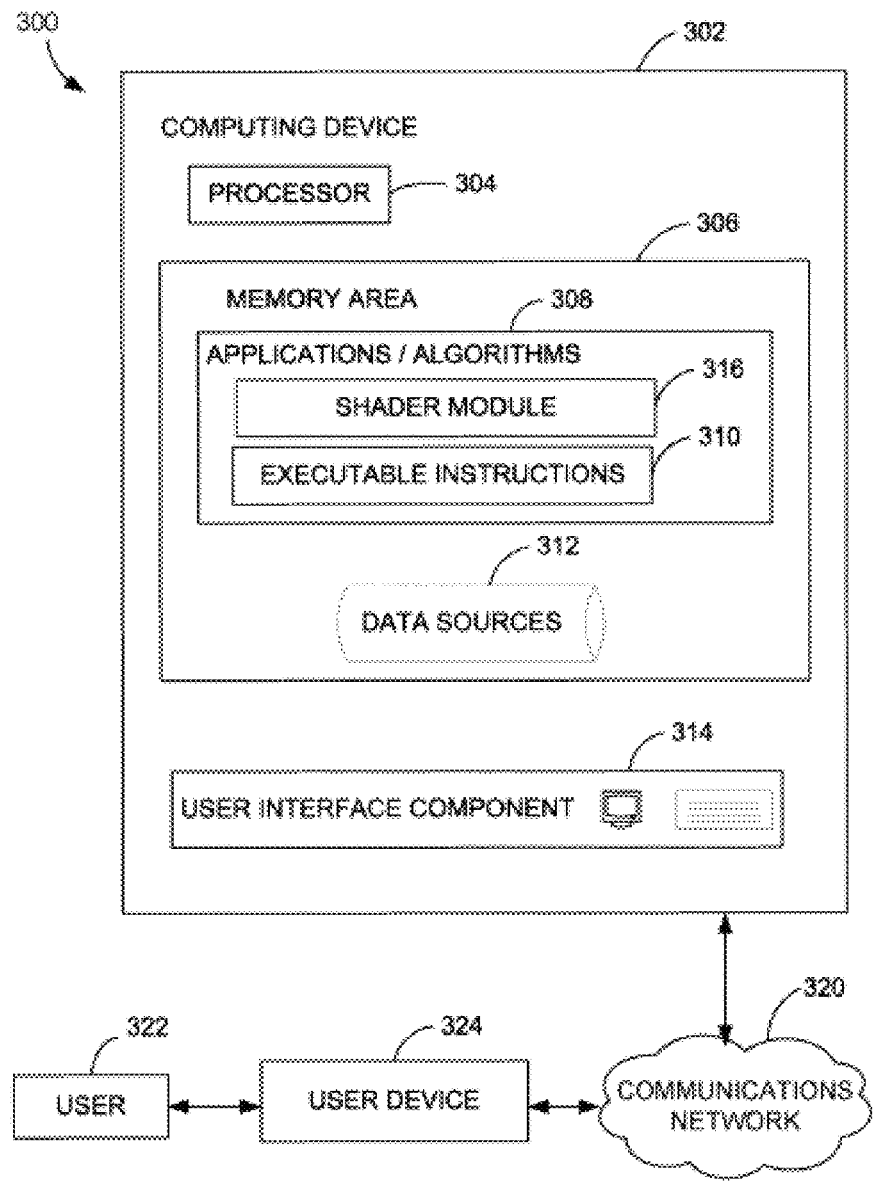
FIG. 7 is a block diagram of an example computing environment that can be implemented as a real-world device or virtual device using some of the various examples disclosed herein.

Turning now to FIG. 7, an exemplary block diagram illustrates a cloud-computing environment for rendering a 3D representation using a 2D object. The architecture 200 illustrates an exemplary cloud-computing infrastructure, suitable for use in implementing aspects of this disclosure. The architecture 200 should not be interpreted as having any dependency or requirement related to any single component or combination of components illustrated therein. In addition, any number of nodes, virtual machines, data centers, role instances, or combinations thereof can be employed to achieve the desired functionality within the scope of embodiments of the present disclosure.

The distributed computing environment of FIG. 7 includes a public network 202, a private network 204, and a dedicated network 206. The public network 202 can be a public cloud-based network of computing resources, for example. The private network 204 can be a private enterprise network or private cloud-based network of computing resources. And the dedicated network 206 can be a third-party network or dedicated cloud-based network of computing resources. In some examples, the private network 204 can host a customer data center 210, and the dedicated network 206 can host cloud shader services 212, which are discussed in more detail below relative to FIG. 8.

The hybrid cloud 208 can include any combination of the public network 202, the private network 204, and the dedicated network 206. For example, the dedicated network 206 can be optional, with the hybrid cloud 208 comprised of the public network 202 and the private network 204. Along these lines, some customers can opt to only host a portion of the customer data center 210 in the public network 202 and/or the dedicated network 206, retaining some of the customers' data or hosting of customer services in the private network 204. For example, a customer that manages healthcare data or stock brokerage accounts can elect or be required to maintain various controls over the dissemination of healthcare or account data stored in its data center or the applications processing such data (e.g., software for reading radiology scans, trading stocks, etc.). Myriad other scenarios exist whereby customers desire or need to keep certain portions of data centers under the customers' own management. Thus, in some examples, customer data centers can use the hybrid cloud 208 in which some data storage and processing is performed in the public network 202 while other data storage and processing is performed in the dedicated network 206.

The public network 202 can include data centers configured to host and support operations, including tasks of a distributed application, according to a fabric controller 218. It will be understood and appreciated that the data center 214 and the data center 216 shown in FIG. 6 are merely examples of suitable implementations for accommodating one or more distributed applications and are not intended to suggest any limitation as to the scope of use or functionality of examples disclosed herein. Neither should the data center 214 and the data center 216 be interpreted as having any dependency or requirement related to any single resource, combination of resources, combination of servers (e.g., servers 220 and 224), combination of nodes (e.g., nodes 232 and 234), or a set of application programming interfaces (APIs) to access the resources, servers, and/or nodes.

The data center 214 illustrates a data center comprising a plurality of servers, such as the servers 220 and 224. The fabric controller 218 is responsible for automatically managing the servers 220 and 224 and distributing tasks and other resources within the data center 214. By way of example, the fabric controller 218 relies on a service model (e.g., designed by a customer that owns the distributed application) to provide guidance on how, where, and when to configure the server 222 and how, where, and when to place the application 226 and the application 228 thereon in some examples. One or more role instances of a distributed application can be placed on one or more of the servers 220 and 224 of the data center 214, where the one or more role instances can represent the portions of software, component programs, or instances of roles that participate in the distributed application. In other examples, one or more of the role instances can represent stored data that are accessible to the distributed application.

The data center 216 illustrates a data center comprising a plurality of nodes, such as the node 232 and the node 234. One or more virtual machines can run on nodes of the data center 216, such as a virtual machine 236 of the node 234 for example. Although FIG. 6 depicts a single virtual node on a single node of the data center 216, any number of virtual nodes can be implemented on any number of nodes of the data center 216 in accordance with illustrative embodiments of the disclosure. Generally, the virtual machine 236 is allocated to role instances of a distributed application, or service application, based on demands (e.g., amount of processing load) placed on the distributed application. As used herein, the phrase "virtual machine" is not meant to be limiting, and can refer to any software, application, operating system, or program that is executed by a processing unit to underlie the functionality of the role instances allocated thereto. Further, the virtual machine(s) 236 can include processing capacity, storage locations, and other assets within the data center 216 to properly support the allocated role instances.

In operation, the virtual machines are dynamically assigned resources on a first node and second node of the data center, and endpoints (e.g., the role instances) are dynamically placed on the virtual machines to satisfy the current processing load. In one instance, a fabric controller 230 is responsible for automatically managing the virtual machines running on the nodes of the data center 216 and for placing the role instances and other resources (e.g., software components) within the data center 216. By way of example, the fabric controller 230 relies on a service model (e.g., designed by a customer that owns the service application) to provide guidance on how, where, and when to configure the virtual machines, such as the virtual machine 236, and how, where, and when to place the role instances thereon in some examples.

As discussed above, the virtual machines can be dynamically established and configured within one or more nodes of a data center. As illustrated herein, the node 232 and the node 234 can be any form of computing devices, such as, for example, a personal computer, a desktop computer, a laptop computer, a mobile device, a consumer electronic device, a server, the computing device 100 of FIG. 5, and the like. In one instance, the nodes 232 and 234 host and support the operations of the virtual machine(s) 236, while simultaneously hosting other virtual machines carved out for supporting other tenants of the data center 216, such as internal services 238 and hosted services 240. Often, the role instances can include endpoints of distinct service applications owned by different customers.

Typically, each of the nodes 232 and 234 include, or is linked to, some form of a computing unit (e.g., central processing unit, microprocessor, etc.) to support operations of the component(s) running thereon. As utilized herein, the phrase "computing unit" generally refers to a dedicated computing device with processing power and storage memory, which supports operating software that underlies the execution of software, applications, and computer programs thereon. In one instance, the computing unit is configured with tangible hardware elements, or machines, that are integral, or operably coupled, to the nodes to enable each device to perform a variety of processes and operations. In another instance, the computing unit can encompass a processor (not shown) coupled to the computer-readable medium (e.g., computer storage media and communication media) accommodated by each of the nodes.

The role of instances that reside on the nodes can be to support operation of service applications, and thus they can be interconnected via APIs. In one instance, one or more of these interconnections can be established via a network cloud, such as the public network 202. The network cloud serves to interconnect resources, such as the role instances, which can be distributed across various physical hosts, such as the nodes 232 and 234. In addition, the network cloud facilitates communication over channels connecting the role instances of the service applications running in the data center 216. By way of example, the network cloud can include, without limitation, one or more communication networks, such as local area networks (LANs) and/or wide area networks (WANs). Such communication networks are commonplace in offices, enterprise-wide computer networks, intranets, and the Internet, and therefore need not be discussed at length herein.

FIG. 7 is a block diagram of an example computing environment 300 that can be implemented as a real-world device or virtual device using some of the various examples disclosed herein. The computing device 302 represents any device executing instructions (e.g., as application programs, operating system functionality, or both) to implement operations and functionality as described herein. The computing device 302 can include a mobile computing device or any other portable device. In some examples, a mobile computing device includes a mobile telephone, laptop, tablet, computing pad, netbook, gaming device, wearable device, head mounted display (HMD) and/or portable media player. The computing device 302 can also represent less portable devices such as desktop personal computers, kiosks, tabletop devices, industrial control devices, wireless charging stations, electric automobile charging stations, and other physical objects embedded with computing resources and/or network connectivity capabilities. Additionally, the computing device 302 can represent a group of processing units or other computing devices.

In some examples, the computing device 302 has at least one processor 304, a memory area 306, and at least one user interface. These can be the same or similar to the processor(s) 114 and memory 112 of FIG. 7, respectively. The processor 304 includes any quantity of processing units and is programmed to execute computer-executable instructions for implementing aspects of the disclosure. The instructions can be performed by the processor or by multiple processors within the computing device, or performed by a processor external to the computing device. In some examples, the processor 304 is programmed to execute instructions such as those that are illustrated in the other figures.

The computing device 302 further has one or more computer readable media such as the memory area 306. The memory area 306 includes any quantity of media associated with or accessible by the computing device. The memory area 306 can be internal to the computing device 302 (as shown in FIG. 7), external to the computing device (not shown), or both (not shown). In some examples, the memory area 306 includes read-only memory and/or memory wired into an analog computing device.

The memory area 306 stores, among other data, one or more applications or algorithms 308 that include data and executable instructions 310. The applications, when executed by the processor, operate to perform functionality on the computing device. Exemplary applications include shader applications and/or components, such as a shader module 316, for example. The applications can communicate with counterpart applications or services such as web services accessible via a network, including a communications network 320. For example, the applications can represent downloaded client-side applications that correspond to server-side services executing in a cloud. In some examples, applications generated can be configured to communicate with data sources and other computing resources in a cloud during runtime, or can share and/or aggregate data between client-side services and cloud services. The memory area 306 can store data sources 312, which represent data stored locally at the memory area 306, data access points stored locally at the memory area 306 and associated with data stored remote from the computing device 302, or any combination of local and remote data in various examples.

The user interface component 314 can include instructions executed by the processor 304 of the computing device 302, and cause the processor 304 to perform operations, including to receive user input, provide output to a user and/or user device, and interpret user interactions with a computing device.

Portions of the user interface component 314 can thus reside within the memory area 306. In some examples, the user interface component 314 includes a graphics card for displaying data to a user 322 and receiving data from the user 322. The user interface component 314 can also include computer-executable instructions (e.g., a driver) for operating the graphics card. Further, the user interface component 314 can include a display (e.g., a touch screen display or natural user interface) and/or computer-executable instructions (e.g., a driver) for operating the display. In some examples, the display can be a 3D display, such as can be found in an HMD. The user interface component 314 can also include one or more of the following to provide data to the user or receive data from the user: a keyboard (physical or touchscreen display), speakers, a sound card, a camera, a microphone, a vibration motor, one or more accelerometers, a Bluetooth® brand communication module, global positioning system (GPS) hardware, and a photoreceptive light sensor. For example, the user can input commands or manipulate data by moving the computing device in a particular way. In another example, the user can input commands or manipulate data by providing a gesture detectable by the user interface component, such as a touch or tap of a touch screen display or natural user interface. In still other examples, a user, such as the user 322, can interact with a separate user device 324, which can control or be controlled by the computing device 302 over the communications network 320, a wireless connection, or a wired connection.

Figure 8:
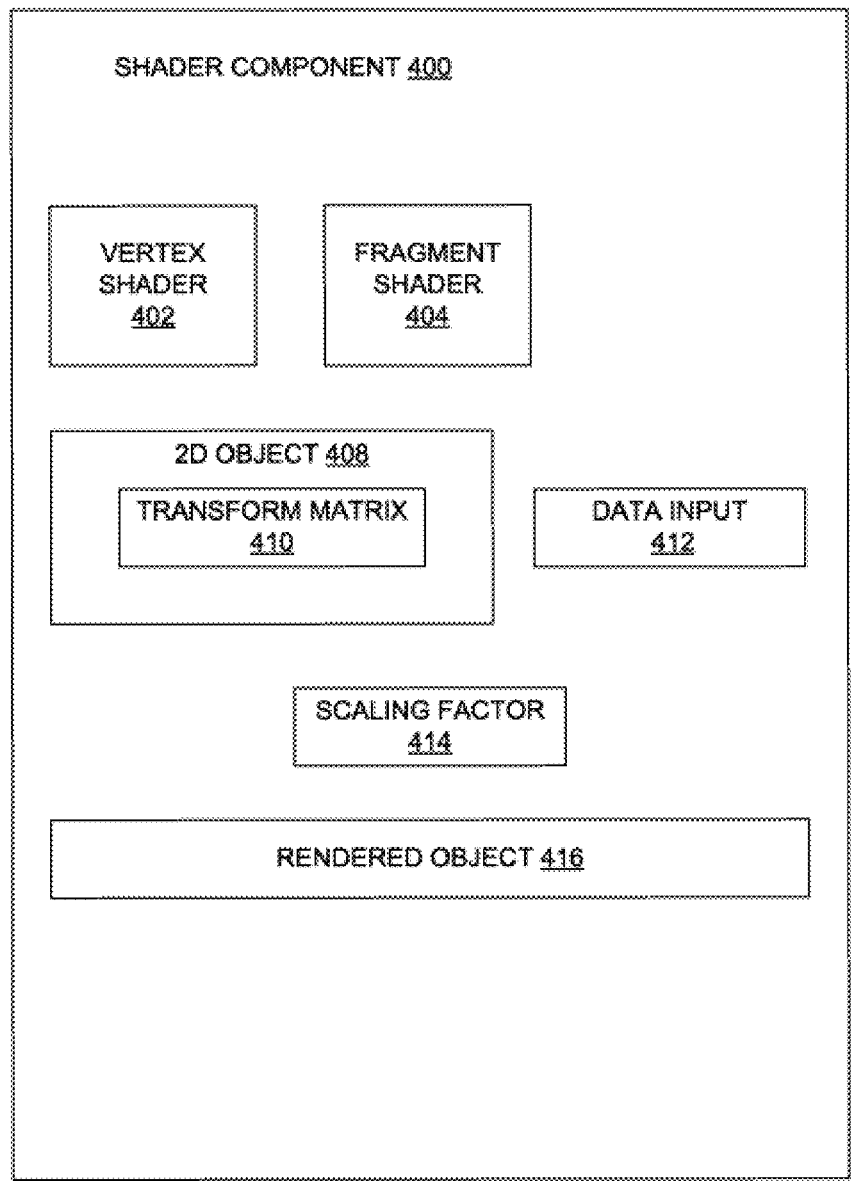
FIG. 8 is a block diagram of a shader component suitable for implementing some of the various examples disclosed herein.
Figure 9:
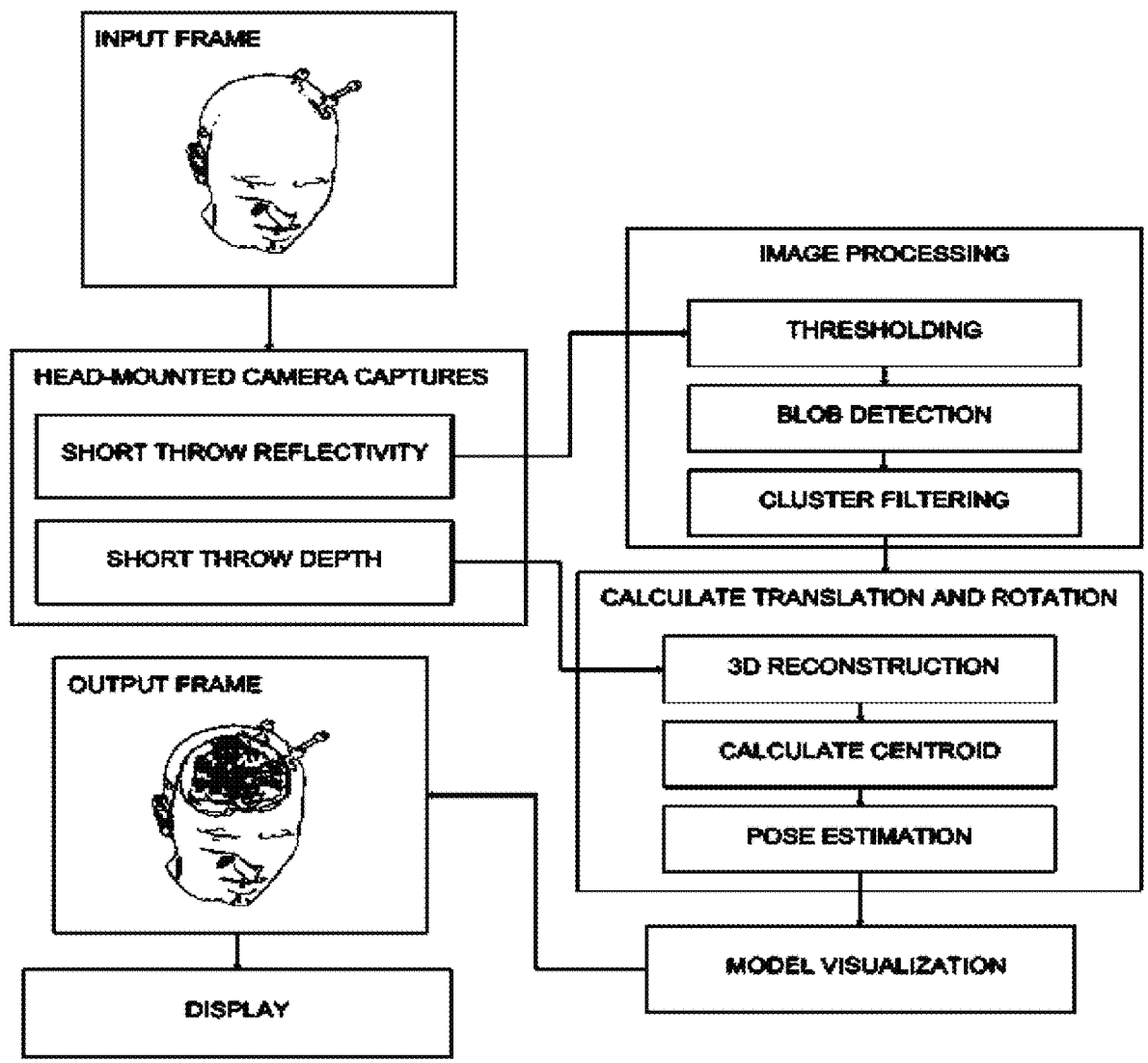
FIG. 9 shows a flowchart for an embodiment of the invention.
Figure 10:
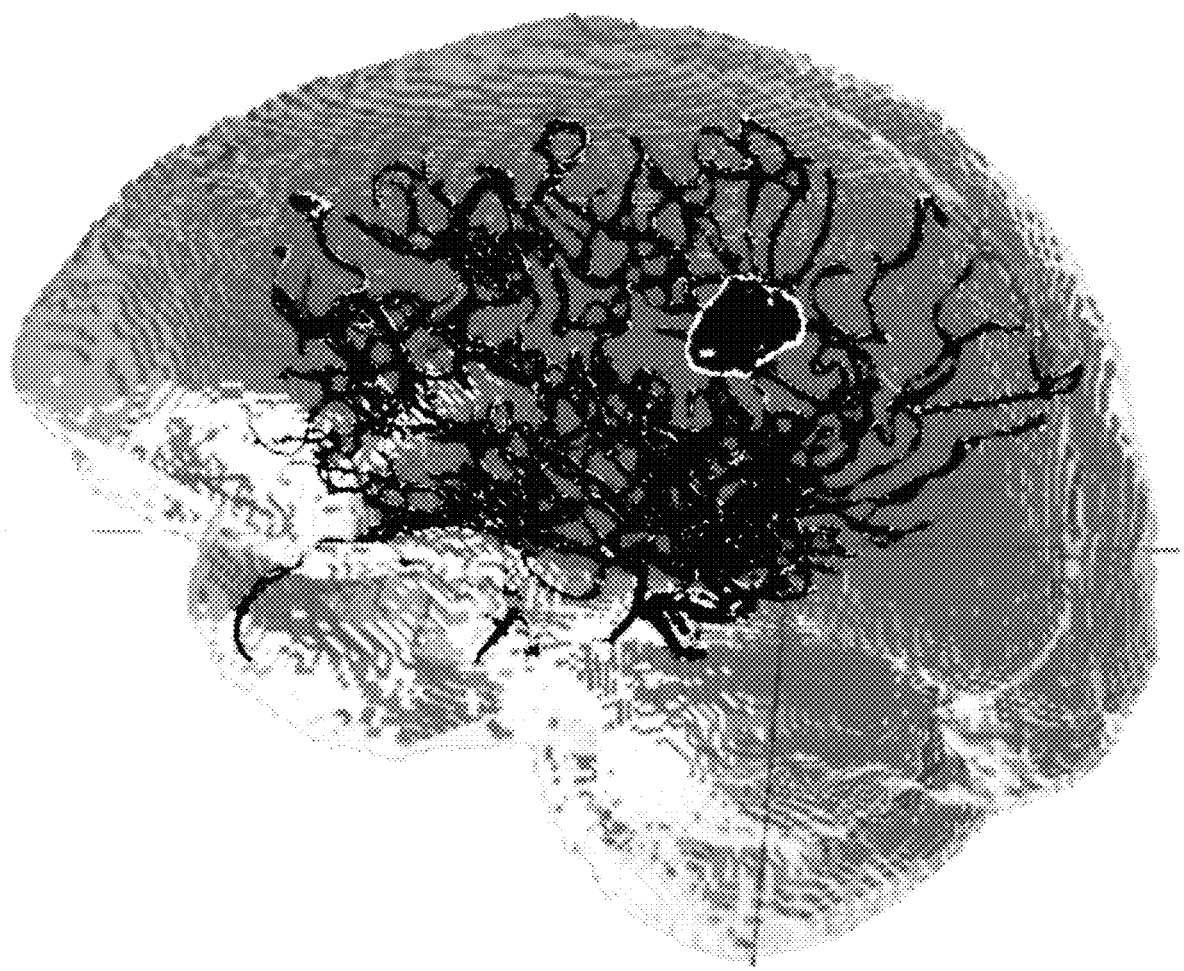
FIG. 10 shows an augmented reality viewport showing the tumor and vasculature projected on the mannequin head, and the user's hand interacting with a user interface.
Figure 11:
FIG. 11 shows a 3D comprehensive visualization superimposed on 3D-printed head.
Figure 12:
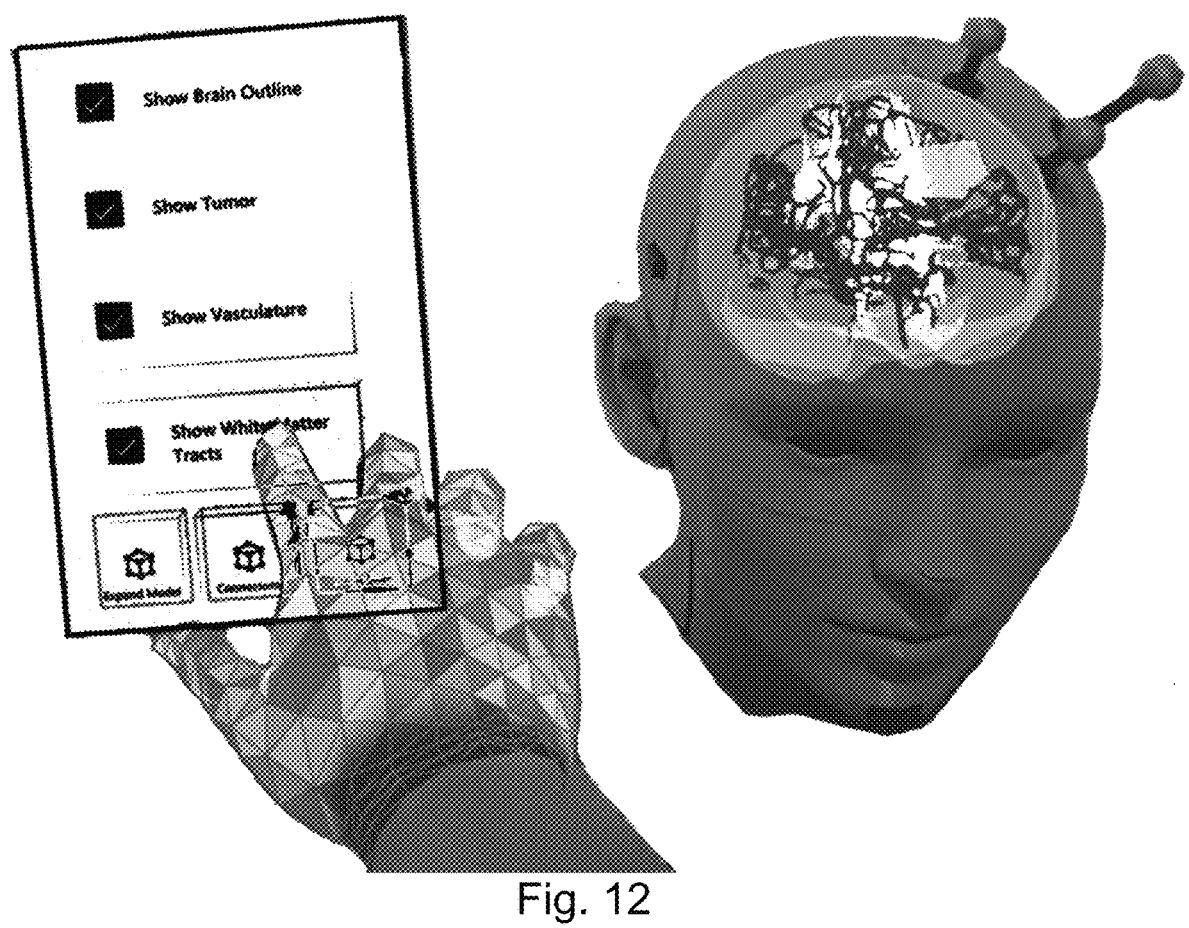
FIG. 12 shows a viewport showing a 3D comprehensive visualization superimposed on 3D-printed head, the user's arm, and a user interface device.

FIG. 8 is a block diagram of a shader component 400 that is suitable for implementing some of the various examples disclosed herein. The shader component 400 can be implemented as a cloud service, in part or in whole, and can further be implemented on one or more computer storage devices having computer-executable instructions stored thereon for rendering "fake" thickness on 2D objects. That is, the shader component 400 can leverage computing environments described in relation to other figures described herein. It should be understood that functionality can be allocated among the different portions in some embodiments differently than is described in this exemplary embodiment.

The shader component 400 includes a vertex shader 402 and a fragment shader 404. The shader component 400 can obtain or receive a 2D object 408. The 2D object 408 can be a 2D geometry, such as a UI element for example, comprising quads, or quad faces. A quad is a component of a mesh used in modeling operations, having four-edge faces with four vertices. Vertex, or vertices, refers to a position in 3D space, along with other data such as color, vector, and texture coordinates, for example. A face, as used herein, is a closed set of edges (such as a triangle face having three edges, or a quad face having four edges). An edge, as used herein, is a connection between two vertices. The 2D object 408 can include a number of different values and/or parameters identified as properties of the 2D object 408 by the shader component 400.

The 2D object 408 includes a transform matrix 410 in some examples. The transform matrix 410 is passed to the vertex shader 402 automatically when the 2D object 408 is obtained by the shader component 400. The transform matrix 410 is associated with the 2D object 408 and includes elements that are used by the vertex shader 402 to define a scaling factor 414 for the 2D object 408. The scaling factor 414 is used by the vertex shader 402 to adjust the thickness of the edge(s) to render.

In some examples, a data input 412 is optionally received by the shader component 400 in association with the 2D object 408. In some examples, the data input 412 includes separate elements defined by developers or users, separately defined parameters for the desired 3D output, and the like. For example, the data input 412 can define the color of a background, or a desired size/scale of an element.

The vertex shader 402 uses one or more logic operations to determine the relative location of a camera, which is used to determine which edge(s) to render to generate the perceived thickness on the quad (or other shape element). The vertex shader 402 determines where the camera is relative to the 2D object 408 (e.g., to the left of the object, to the right of the object, upper left quadrant, lower left quadrant, etc.) and which vertices of the quad lie on the same side with the camera, indicating that the corresponding edges should be visible. In other words, the vertex shader 402 transforms the camera's world position into the quad's local position, then uses logic operations to determine which side of the quad the camera is located on to decide which edge on the quad to draw. As an example, assume the "pos.x" value is larger than zero (0), such a 0.50 for example, indicating the vertices lie on the right side of the quad, and the first test function returns "1". In the second test function, if the camera's x position (oCamPos.x) is larger than 0.5 which is the quad's right most border, the function returns "1", indicating the camera lies on the right side of the quad. The product of these two functions returns "1" only when the above two test functions return "1", indicating vertices on the right side of the quad is visible. This value is stored in the "x" part of a vector4 value "o.show".

As another example, assume the "pos.x" value is less than zero (0), such as −0.50 for example, indicating the vertices lie on the left side of the quad and the first test function returns "0". In the second test function, if the camera's x position (oCamPos.x) is larger than 0.5 which is the quad's right most border, the function returns "1", indicating the camera lies on the right side of the quad. The product of these two functions returns "0", indicating vertices on the left side of the quad is invisible. This value is stored in the "z" part of a vector4 value "o.show". The vertex shader 402 returns a visibility value that indicates visibility of each edge of a quad, where a value of 0 is not visible and a value of 1 is visible. The vertex shader 402 uses the visibility value to render only visible edges.

In addition to determining which edge(s) to render, the vertex shader 402 determines a thickness of the edge(s) to be drawn. The vertex shader 402 uses a dot product operation to calculate the cosine of horizontal and vertical angles between the viewing vector and the quad's normal vector, to determine the thickness of the edge(s) to be drawn in some examples. This result is further filtered by the visibility value in order to only render viewable edges. In these examples, the dot product operation between vectors is the sum of the product of each corresponding element of the two vectors, where the first vector is the viewing vector of the camera and the second vector is where the object is facing in space. These two vectors are normalized so that the dot product of these vectors is the cosine of the angle that is used to derive how much of the object is facing the camera, and that cosine value is used to determine the width of the edge to render.

As another example, if the object is viewed head on, or straight on, the viewing angle is 0 degree, and the dot product is 1, subtracting 1, gives 0, indicating zero thickness. If the viewing angle is from a sharp angle, or almost the side of the object, the viewing angle is 90 degrees, and the dot product is 0, subtracting 1, gives 1, indicating full thickness. Since the dot product is a continuous function, as the viewing angle changes from 0 to 90 degrees, the result given by one minus the dot product changes from 0 to 1 in a continues manner, indicating the edge changes from 0 thickness, increasing to some thickness, and finally to full thickness.

The determined thickness of the edges, filtered by the determined visibility, is modified by the vertex shader 402 to compensate for the scaling factor so that the thickness of the edge(s) is/are independent of the quad scale, the scaling factor being derived from the transform matrix of the 2D object.

The fragment shader 404 uses the scaled result values to render colors for parts of the quad that are visible based on the viewing angle determined by vertex shader 402. The fragment shader 404 renders horizontal edge colors and vertical edge colors separately, to emulate lighting conditions. A smoothstep function is utilized to produce a smoothing result in some examples. As a result, anti-aliased edges of the quad are added, and the visibility, thickness, and color all follow the same rule of 3D geometry, while being rendered on a 2D card.

For example, the quad is rendered with a solid color, using values output from the vertex shader 402 (i.e., solid.zw) to determine whether and at which place to draw the edges, or frame, and this information is used to interpolate the edge color and background color. The edge colors are separately determined for vertical and horizontal edges. The fragment shader 404 determines whether a pixel's position is above or below a threshold. If the pixel's position is determined to be above the threshold, the fragment shader 404 renders the pixel with the frame color; if the pixel's position is determined to be below the threshold, the pixel is rendered with the background color.

The rendered object 416 can be output to MR devices or to another computing device, can be used for UI elements (e.g., a background of a button) or objects rendered in a VR or MR environment (e.g., a virtual painting displayed on a wall in MR). The rendered object 416 can be packaged into an application file that is loaded into a MR device, in some examples. In other examples, the shader component 400 can be launched from a VR/MR device and run in real-time to display objects in the VR/MR world as the viewing angles and object angles dynamically change.

Figure 13:
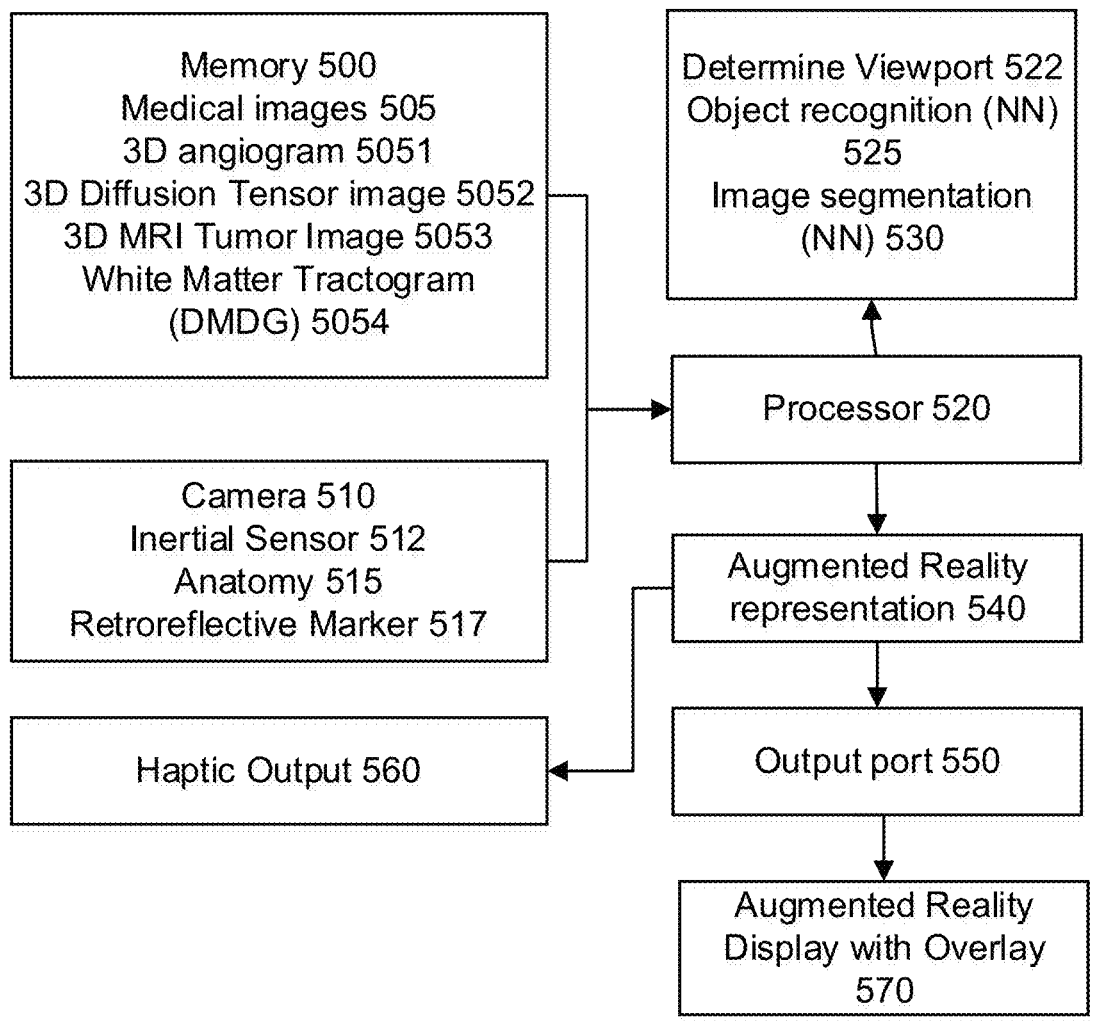
FIG. 13 shows a block diagram of a system embodiment of the invention.
Figure 14:
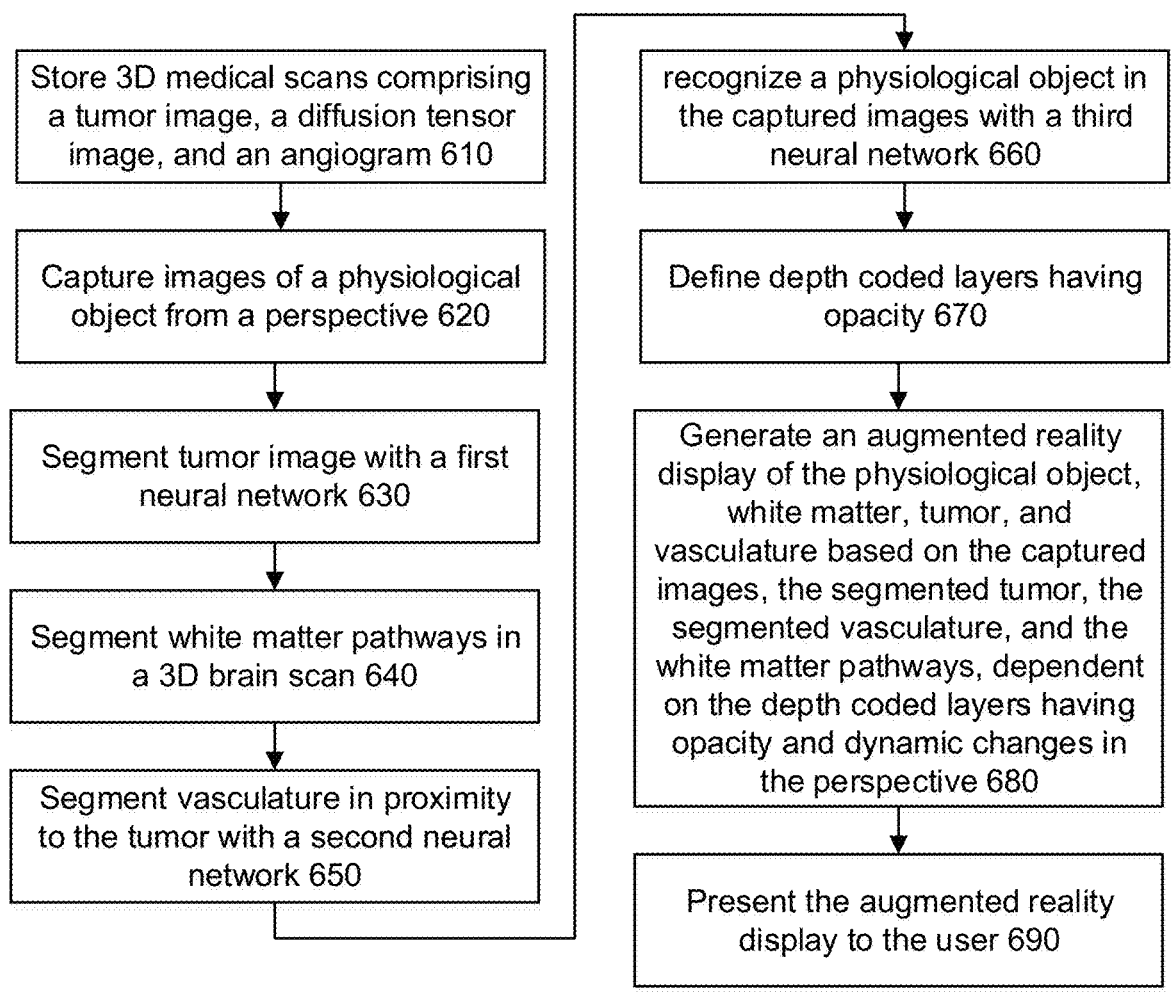
FIG. 14 shows a flowchart of a method according to the invention.

FIG. 13 shows a system according to an embodiment of the invention. The system includes a memory system 500 which stores medical images 505, which may be one or more of 3D angiogram images 5051, 3D diffusion tensor images 5052, 3D MRI tumor images 5053, and white matter tractograms (DMDG) 5054. The system also includes real world sensors, such as a camera 510 to view anatomy 515, an inertial sensor 512, and a retroreflective marker 517 which provides a readily recognized visual reference in the images from the camera 510.

A processor 520 performs various functions, including determining a viewport 522, recognizing an object 525, and image segmentation 530 of the various medical images, such as angiogram, tumor MRI, and tractogram. The segmentation may employ various types of neural networks, statistical processes, or logical processing. The processor also generates a representation of an augmented reality image 540, and more particularly the overlay registered with the actual viewport od the user. The augmented reality representation 540 is then passed through an output port 550, and presented through an augmented reality display with overlay 570. The augmented reality representation 540 may also control a haptic output 560.

An augmented reality method is provided, which stores 3D medical scans comprising a tumor image, a diffusion tensor image, and an angiogram 610. Images of a physiological object are captured from a perspective 620. The tumor image is automatically segmented with a first neural network 630. White matter pathways in a 3D brain scan are automatically segmented 640. Vasculature in proximity to the tumor is automatically segmented with a second neural network 650. A physiological object in the captured images is automatically recognized with a third neural network 660. Depth coded layers having opacity are then defined 670. An augmented reality display of the physiological object, white matter, tumor, and vasculature is then generated based on the captured images, the segmented tumor, the segmented vasculature, and the white matter pathways, dependent on the depth coded layers having opacity and dynamic changes in the perspective 680. The augmented reality display is then presented to the user 690.

When introducing elements of aspects of the disclosure or the examples thereof, the articles "a," "an," "the," and "said" are intended to mean that there are one or more of the elements. The terms "comprising," "including," and "having" are intended to be inclusive and mean that there can be additional elements other than the listed elements. The term "exemplary" is intended to mean "an example of." The phrase "one or more of the following: A, B, and C" means "at least one of A and/or at least one of B and/or at least one of C."

Any range or device value given herein can be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above can relate to one embodiment or can relate to several embodiments. The embodiments are not limited to those that solve any or all of the stated problems or those that have any or all of the stated benefits and advantages. It will further be understood that reference to 'an' item refers to one or more of those items.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

While the disclosure is susceptible to various modifications and alternative constructions, certain illustrated examples thereof are shown in the drawings and have been described above in detail. It should be understood, however, that there is no intention to limit the disclosure to the specific forms disclosed, but on the contrary, the intention is to cover all modifications, alternative constructions, and equivalents falling within the spirit and scope of the disclosure.

REFERENCES

Each reference and patent cited herein is expressly incorporated herein by reference in its entirety, for all purposes.

Ayoub, Ashraf, and Yeshwanth Pulijala. "The application of virtual reality and augmented reality in Oral & Maxillofacial Surgery." BMC Oral Health 19 (2019): 1-8.

Best, J. (2018). Augmented reality in the operating theater: How surgeons are using Microsoft's HoloLens to make operations better. ZDNET.

*Brain Tumor: Statistics.* (2022). Cancer.Net. www.cancer.net/cancer-types/brain-tumor/statistics Chidambaram, Swathi, Vito Stifano, Michelle Demetres, Mariano Teyssandier, Maria Chiara Palumbo, Alberto Redaelli, Alessandro Olivi, Michael L J Apuzzo, and Susan C. Pannullo. "Applications of augmented reality in the neurosurgical operating room: a systematic review of the literature." Journal of Clinical Neuroscience 91 (2021): 43-61.

Djenouri, Youcef, Asma Belhadi, Gautam Srivastava, and Jerry Chun-Wei Lin. "Secure collaborative augmented reality framework for biomedical informatics." IEEE Journal of Biomedical and Health Informatics 26, no. 6 (2021): 2417-2424.

Fick, Tim, Jesse A M van Doormaal, Lazar Tosic, Renate J. van Zoest, Jene W. Meulstee, Eelco W. Hoving, and Tristan P C van Doormaal. "Fully automatic brain tumor segmentation for 3D evaluation in augmented reality." Neurosurgical focus 51, no. 2 (2021): E14.

Gonzalez Izard, Santiago, Juan A. Juanes Méndez, Pablo Ruisoto Palomera, and Francisco J. García-Peñalvo. "Applications of virtual and augmented reality in biomedical imaging." Journal of medical systems 43 (2019): 1-5.

Haouchine, Nazim, Parikshit Juvekar, Michael Nercessian, William M. Wells III, Alexandra Golby, and Sarah Frisken. "Pose estimation and non-rigid registration for augmented reality during neurosurgery." IEEE Transactions on Biomedical Engineering 69, no. 4 (2021): 1310-1317.

Hollon, Todd C., Balaji Pandian, Arjun R. Adapa, Esteban Urias, Akshay V. Save, Siri Sahib S. Khalsa, Daniel G. Eichberg et al. "Near real-time intraoperative brain tumor diagnosis using stimulated Raman histology and deep neural networks." Nature medicine 26, no. 1 (2020): 52-58.

Huang, James, Martin Halicek, Maysam Shahedi, and Baowei Fei. "Augmented reality visualization of hyperspectral imaging classifications for image-guided brain tumor phantom resection." In Medical Imaging 2020: Image-Guided Procedures, Robotic Interventions, and Modeling, vol. 11315, pp. 206-215. SPIE, 2020.

Jasenovcova, L. (2022). *What is augmented reality and how does AR work.* Resco. www.resco.net/blog/what-is-augmented-reality-and-how-does-ar-work/

Johns Hopkins Performs Its First Augmented Reality Surgeries in Patients. (2021). Johns Hopkins Medicine. www.hopkinsmedicine.org/news/articles/johns-hopkins-performs-its-first-augmented-reality-surgeries-in-patients Jud, Lukas, Javad Fotouhi, Octavian Andronic, Alexander Aichmair, Greg Osgood, Nassir Navab, and Mazda Farshad. "Applicability of augmented reality in orthopedic surgery-a systematic review." BMC musculoskeletal disorders 21, no. 1 (2020): 1-13. bmcmusculoskeletdisord.biomedcentral.com/articles/10.1186/s12891-020-3110-2

Le, J. (2021). *How to do Semantic Segmentation using Deep Learning.* Nanonets. nanonets.com/blog/how-to-do-semantic-segmentation-using-deep-learning/

Lee, Chester, and George Kwok Chu Wong. "Virtual reality and augmented reality in the management of intracranial tumors: a review." Journal of Clinical Neuroscience 62 (2019): 14-20.

Lee, Tae-Ho, Viduranga Munasinghe, Yan-Mei Li, Jiajie Xu, Hyuk-Jae Lee, and Jin-Sung Kim. "GAN-Based Medical Image Registration for Augmented Reality Applications." In 2022 IEEE 4th International Conference on Artificial Intelligence Circuits and Systems (AICAS), pp. 279-282. IEEE, 2022.

Liu, Tao, Yonghang Tai, Chengming Zhao, Lei Wei, Jun Zhang, Junjun Pan, and Junsheng Shi. "Augmented reality in neurosurgical navigation: a survey." The International Journal of Medical Robotics and Computer Assisted Surgery 16, no. 6 (2020): 1-20.

Lungu, Abel J., Wout Swinkels, Luc Claesen, Puxun Tu, Jan Egger, and Xiaojun Chen. "A review on the applications of virtual reality, augmented reality and mixed reality in surgical simulation: an extension to different kinds of surgery." Expert review of medical devices 18, no. 1 (2021): 47-62.

Malhotra, Priyanka, Sheifali Gupta, Deepika Koundal, Atef Zaguia, and Wegayehu Enbeyle. "Deep neural networks for medical image segmentation." Journal of Healthcare Engineering 2022 (2022).

McKnight, R. Randall, Christian A. Pean, J. Stewart Buck, John S. Hwang, Joseph R. Hsu, and Sarah N. Pierrie. "Virtual reality and augmented reality-translating surgical training into surgical technique." Current Reviews in Musculoskeletal Medicine 13 (2020): 663-674.

Meola, A., Cutolo, F., Carbone, M., Cagnazzo, F., Ferrari, M., & Ferrari, V. (2017). Augmented Reality in Neurosurgery: A Systematic Review. Neurosurgical Review, 40(4), 537-548. doi.org/10.1007/s10143-016-0732-9

Mikhail, Mirriam, Karim Mithani, and George M. Ibrahim. "Presurgical and intraoperative augmented reality in neuro-oncologic surgery: clinical experiences and limitations." World neurosurgery 128 (2019): 268-276.

*Minimally Invasive Brain Tumor Surgery.* (2022). Pacific Neuroscience Institute. www.pacificneuroscienceinstitute.org/brain-tumor/treatment/minimally-invasive-brain-surgery/ #tab-gravity-assisted Montemurro, Nicola, Sara Condino, Marina Carbone, Nadia Cattari, Renzo D'Amato, Fabrizio Cutolo, and Vincenzo Ferrari. "Brain Tumor and Augmented Reality: New Technologies for the Future." International Journal of Environmental Research and Public Health 19, no. 10 (2022): 6347.

Ponnusamy, Vijayakumar, J. Christopher Clement, K. C. Sriharipriya, and Sowmya Natarajan. "Smart healthcare technologies for massive internet of medical things." In Efficient Data Handling for Massive Internet of Medical Things: Healthcare Data Analytics, pp. 71-101. Chain: Springer International Publishing, 2021.

Salehahmadi, F., & Hajialiasgari, F. (2019). Grand Adventure of Augmented Reality in Landscape of Surgery. *World Journal of Plastic Surgery*, 8(2). doi.org/10.29252/wjps.8.2.135

Satoh, Makoto, Takeshi Nakajima, Takashi Yamaguchi, Eiju Watanabe, and Kensuke Kawai. "Evaluation of augmented-reality based navigation for brain tumor surgery." Journal of Clinical Neuroscience 94 (2021): 305-314.

Siegel, R., L., Miller, K., D., Fuchs, H., E., & Jemal, A. (2021). Cancer Statistics 2021. Cancer *Journal for Clinicians*, 71(1), 7-33. doi.org/10.3322/caac.21654

*Surgery for Brain Tumours*. (2019). Cancer Research UK. www.cancerresearchuk.org/about-cancer/brain-tumours/treatment/surgery/remove-brain-tumour van Doormaal, Jesse A M, Tim Fick, Meedie Ali, Mare Köllen, Vince van der Kuijp, and Tristan P C van Doormaal. "Fully automatic adaptive meshing based segmentation of the ventricular system for augmented reality visualization and navigation." World Neurosurgery 156 (2021): e9-e24.

*What is Deep Learning?* (n.d.). Mathworks. Retrieved Sep. 26, 2022 from www.mathworks.com/discovery/deep-learning.html

*What is SLAM (Simultaneous Localization and Mapping)?* (n.d.). Geoslam. Retrieved Sep. 26, 2022 from geoslam/us/what-is-slam/ www.zdnet.com/article/augmented-reality-in-the-operating-theatre-how-surgeons-are-using-microsofts-hololens-to-make/

Patent Nos. AU-2022252723; CA-3107582; CA-3176333; CN-102842122; CN-110338852; CN-111260786; CN-112043378; CN-113796956; CN-113993475; CN-113994380; CN-114948199; CN-115049806; EP-3443888; EP-3443924; EP-3498212; EP-3726466; EP-3790491; EP-3826525; EP-3847628; EP-3920081; EP-3971907; EP-3993743; EP-4069129; FR-3110763; FR-3110764; JP-2021194544; JP-2022538906; KR-102180135; KR-102395505; KR-20200041697; KR-20210014705; KR-20220038361; KR-20230013041; KR-20230013042; TW-202248962; TW-1786667; U.S. Ser. No. 10/937,542; U.S. Ser. No. 11/071,647-B2; U.S. Ser. No. 11/278,359-B2; US-20100240988; US-20190011703; US-20190142519; US-20190175285; US-20190192230; US-20200168334; US-20200327721; US-20200405397; US-20210045838; US-20210103340; US-20210145642; US-20210161596; US-20210201565; US-20210307841; US-20210361483; US-20220062047; US-20220148459; US-20220346884; US-20230027518; WO-2019165430; WO-2019217893; WO-2020023740; WO-2020056532; WO-2021003304; WO-2021112988; WO-2021214750; WO-2021234304; WO-2021234305; WO-2021245212; WO-2021252384; WO-2022014255; WO-20220200572; WO-2022060409; WO-2022079251; and WO-2023004299.

What is claimed is:

1. An augmented reality system for treating a tumor, comprising:
a memory configured to store at least one type of medical image of an anatomical region comprising the tumor;
at least one camera configured to capture images of anatomy from a dynamically changing perspective;
at least one processor configured to:
receive the images of the at least one type of medical image;
receive the captured images;
segment the at least one type of medical image;
recognize the anatomical region in the captured images using a trained artificial neural network; and
generate an augmented reality representation of the at least one type of medical image of the anatomical region merged with the anatomy from the dynamically changing perspective, wherein the tumor is visually distinguished from non-tumor tissue in the anatomical region;
an output port configured to present the augmented reality representation; and
a haptic output configured to produce proprioceptive stimulation corresponding to a virtual boundary condition according to the segmented at least one type of medical image.

2. The augmented reality system according to claim 1, wherein the at least one type of medical image comprises at least one of:
(1) a 3D angiogram type of medical image,
(2) a 3D diffusion tensor image, and
(3) a 3D tumor type of medical image,
wherein the at least one type of medical image is segmented by a plurality of segmenting neural networks comprising a first segmenting neural network configured to distinguish vascular tissue from nonvascular tissue, and a second segmenting neural network configured to distinguish tumor tissue from nontumor tissue.

3. The augmented reality system according to claim 1, wherein the at least one type of medical image comprises a white matter tractogram.

4. The augmented reality system according to claim 3, wherein the white matter tractogram is based on a diffusion tensor image, and the at least one processor is further configured to reconstruct a 3D model of the white matter tracts from the diffusion tensor image using a Deterministic Maximum Direction Getter (DMDG) algorithm.

5. The augmented reality system according to claim 1, wherein the anatomical region is a cranium; and the least one type of medical image comprises:
a first type of medical image selected from the group consisting of at least one of a magnetic resonance angiogram and a computed tomography angiogram;
a second type of medical image comprising a magnetic resonance image which visualizes a tumor; and
a third type of medical image comprising a diffusion tensor image.

6. The augmented reality system according to claim 1, wherein the at least one processor is configured to segment the at least one type of medical image with a segmenting neural network comprising:
a 3D U-NET, having at least a convolutional neural network;
an encoder comprising a plurality of layers of convolutions, with max pooling over multiple convolution layers; and
a decoder comprising a plurality of layers of convolutions with up-convolutions or transpose convolutions over multiple convolution layers.

7. The augmented reality system according to claim 1, wherein the trained artificial neural network comprises a Reverse Edge Attention network (RE-NET) with skip connections, with a Reverse Edge Attention Module (REAM) embedded in each skip connection.

8. The augmented reality system according to claim 1, wherein the at least one processor is further configured to:
generate the augmented reality representation by recognition of at least one physical marker of the anatomical region;
register the anatomical region comprising the tumor of the at least one type of medical image with the images of anatomy by the at least one camera based on the at least one physical marker; and
superimpose the segmented at least one type of medical image on the captured images dependent on the registration.

9. The augmented reality system according to claim 1, wherein the at least one processor is further configured to recognize at least one retroreflective marker on a surface of the anatomical region, and to dynamically track a position and an orientation of the anatomical region with respect to the at least one camera based on the recognized at least one retroreflective marker.

10. The augmented reality system according to claim 1, further comprising a head-mounted graphical interface having a hand-tracking subsystem.

11. An augmented reality system for treating a brain tumor, comprising:
a memory configured to store data from a 3D model of a white matter tractogram based on diffusion tensor imaging, and a volumetric medical image comprising characteristics of an anatomical region comprising a tumor;
an augmented reality user interface comprising at least one camera configured to capture images of anatomy from a viewport having a dynamically changing perspective, at least one inertial sensor, and a display configured to overlay a computer generated image on a live image;
at least one automated processor, configured to:
retrieve the 3D model and the volumetric medical image from the memory;
segment the volumetric medical image;
recognize the anatomy, and a location and an orientation of the anatomy in the viewport in realtime using a trained artificial neural network;
generate an augmented reality representation of the 3D model and the volumetric medical image merged with the anatomy from the dynamically changing perspective, wherein a visualization of boundaries of the tumor overlays a representation of the recognized anatomy in the viewport; and
control the augmented reality user interface to present an augmented reality presentation comprising the tumor, to thereby facilitate a surgical procedure to treat the tumor.

12. The augmented reality system according to claim 11, wherein the volumetric medical image comprises a white matter track image.

13. The augmented reality system according to claim 12, wherein the at least one automated processor is configured to segment at least one of the 3D model and the volumetric medical image using at least one neural network, and to overlay the segmented volumetric medical images on the recognized anatomy in the viewport.

14. The augmented reality system according to claim 13, wherein the volumetric medical image comprises a 3D angiogram, and the at least one automated processor is further configured to segment the 3D angiogram to distinguish arteries, segment the 3D model to distinguish the brain tumor, label elements as foreground and background, and to apply obscuring logic based on relative depth.

15. The augmented reality system according to claim 14, wherein the at least one automated processor is further configured to segment the 3D angiogram and to segment the 3D model of the brain tumor with a 3D U-NET, having at least a convolutional neural network, an encoder with max pooling, and a decoder with up-convolutions or transpose convolutions, wherein the 3D U-NET further comprises skip connections, which transfer a convoluted image to the equally sized layers across a U-structure, skipping a portion of the encoder and decoder.

16. The augmented reality system according to claim 15, wherein the object recognition neural network comprises a Reverse Edge Attention network (RE-NET) with skip connections, having a Reverse Edge Attention Module (REAM) embedded in each skip connection.

17. The augmented reality system according to claim 16, wherein the at least one automated processor is further configured to process the stored data to reconstruct the 3D model of the white matter tractogram from diffusion tensor magnetic resonance imaging using a Deterministic Maximum Direction Getter (DMDG) algorithm.

18. The augmented reality system according to claim 17, wherein the at least one automated processor is further configured to recognize at least one visible physical marker of the anatomy, and superimpose the segmented 3D model and the volumetric medical image on the captured images of the anatomy.

19. The augmented reality system according to claim 11, wherein the volumetric medical comprises an angiogram, further comprising a haptic user interface configured to provide tactile feedback to a user representing at least segmentation boundaries of at least one of blood vessels and white matter tracts.

20. An augmented reality method, comprising:
storing 3D medical scans comprising a tumor image, a diffusion tensor image, and an angiogram;
capturing images of a physiological object from a perspective;
automatically segmenting the tumor image with a first neural network to distinguish a tumor boundary;
automatically segmenting white matter pathways based on at least the diffusion tensor image;
automatically segmenting vasculature in proximity to the tumor with a second neural network based on at least the angiogram;
automatically recognizing a physiological object in the captured images with a third neural network;
defining depth coded layers comprising the tumor having opacity;
generating an augmented reality display of the physiological object, white matter, tumor, and vasculature based on the captured images, the segmented tumor image, the segmented vasculature, and the white matter pathways, dependent on the depth coded layers having opacity and dynamic changes in the perspective; and
presenting the augmented reality display to the user.

* * * * *